United States Patent
Kato

(10) Patent No.: US 10,352,692 B1
(45) Date of Patent: Jul. 16, 2019

(54) SURFACE ROUGHNESS DETERMINATION APPARATUS USING A WHITE LIGHT SOURCE AND DETERMINATION METHOD

(71) Applicant: PaPaLaB Co., Ltd., Hamamatsu-shi, Shizuoka (JP)

(72) Inventor: Makoto Kato, Hamamatsu (JP)

(73) Assignee: PAPALAB CO., LTD., Hamamatsu-shi (JP)

( * ) Notice: Subject to any disclaimer, the term of this patent is extended or adjusted under 35 U.S.C. 154(b) by 0 days.

(21) Appl. No.: 15/899,851

(22) Filed: Feb. 20, 2018

(51) Int. Cl.
    G01B 11/00     (2006.01)
    G01F 9/00      (2006.01)
    (Continued)

(52) U.S. Cl.
    CPC ......... *G01B 11/30* (2013.01); *G01N 21/8806* (2013.01); *G06F 9/3001* (2013.01); *G06T 7/0004* (2013.01)

(58) Field of Classification Search
    None
    See application file for complete search history.

(56) References Cited

U.S. PATENT DOCUMENTS 4,145,140 A * 3/1979 Fujii ............... G01B 11/303
                                                356/512
5,155,558 A * 10/1992 Tannenbaum ....... G01N 21/57
                                                348/128
(Continued)

FOREIGN PATENT DOCUMENTS

JP    6-307840 A    11/1994
JP    2556556 A      9/1996
(Continued)

*Primary Examiner* — Kara E. Geisel
*Assistant Examiner* — Jarreas C Underwood
(74) *Attorney, Agent, or Firm* — Brundidge & Stanger, P.C.

(57) ABSTRACT

Object:
An object is to quantify the roughness of a test surface by scattering and diffraction of illumination light and to evaluate the matching degree of surface roughness separately from color based on a difference in roughness.
Solution to Problem
A surface roughness determination apparatus 1 using a white light source includes an arithmetic processing unit 3 configured to convert 3-band visual sensitivity images S1$i$, S2$i$ and S3$i$, which respectively have three spectral sensitivities (S1($\lambda$), S2($\lambda$) and S3($\lambda$)) subjected to linear transformation so as to be equivalent to a CIE XYZ color matching function and are obtained from a surface 5 by a two-dimensional colorimeter 2 using the three spectral sensitivities (S1($\lambda$), S2($\lambda$) and S3($\lambda$)), into tristimulus values X, Y and Z in a CIE XYZ color system and perform arithmetic operations. This arithmetic processing unit 3 includes a color difference calculator configured to calculate a color difference $\Delta E$; a color space histogram distribution creator configured to divide an examination area of coordinates corresponding to a color space in the XYZ color system by grids G and respectively integrate the numbers of pixels on a test surface and on a reference surface included in each of the grids G, so as to create color space histogram distributions in the XYZ color system; a surface roughness index calculator configured to calculate a surface roughness index M indicating a difference between the two color space histogram distributions of the test surface and the reference surface with or without an offset correction; a surface roughness measurement data storage unit configured to store a measured surface roughness value Ra actually measured by a roughness meter; and a function setter configured to set at (Continued)

least one of a first calibration curve function L1 indicating a correlation of the measured surface roughness value Ra to a surface roughness evaluation index Est, a second calibration curve function L2 indicating a correlation of the measured surface roughness value Ra to the color difference ΔE, a third calibration curve function L3 indicating a correlation of the measured surface roughness value Ra to the surface roughness index M calculated without the offset correction and a fourth calibration curve function indicating a correlation of the measured surface roughness value Ra to the surface roughness index M calculated with the offset correction.

6 Claims, 39 Drawing Sheets

(51) Int. Cl.
*G01N 21/00* (2006.01)
*G01B 11/30* (2006.01)
*G06F 9/30* (2018.01)
*G06T 7/00* (2017.01)
*G01N 21/88* (2006.01)

(56) References Cited

U.S. PATENT DOCUMENTS

| | | | | |
|---|---|---|---|---|
| 5,748,318 A | * | 5/1998 | Maris | G01N 21/1702 |
| | | | | 356/630 |
| 5,850,472 A | * | 12/1998 | Alston | G01J 3/10 |
| | | | | 382/162 |
| 8,300,234 B2 | * | 10/2012 | Debevec | G01N 21/55 |
| | | | | 356/600 |
| 2002/0085751 A1 | * | 7/2002 | Matsushiro | H04N 1/60 |
| | | | | 382/162 |
| 2003/0011596 A1 | * | 1/2003 | Zhang | G06T 15/506 |
| | | | | 345/426 |

FOREIGN PATENT DOCUMENTS

| | | | | |
|---|---|---|---|---|
| JP | 2001-4351 | A | | 1/2001 |
| JP | 2006-162558 | | * | 6/2006 |
| JP | 4204879 | B | | 10/2008 |
| JP | 2011-031370 | A | | 2/2011 |
| JP | 2011-69688 | A | | 4/2011 |
| JP | 2014-032177 | A | | 2/2014 |
| JP | 2014-081324 | A | | 5/2014 |
| JP | 2014-149286 | | * | 8/2014 |
| JP | 2015-143666 | A | | 8/2015 |
| JP | 2015-169641 | A | | 9/2015 |
| JP | 2018-128436 | | * | 8/2018 |

* cited by examiner

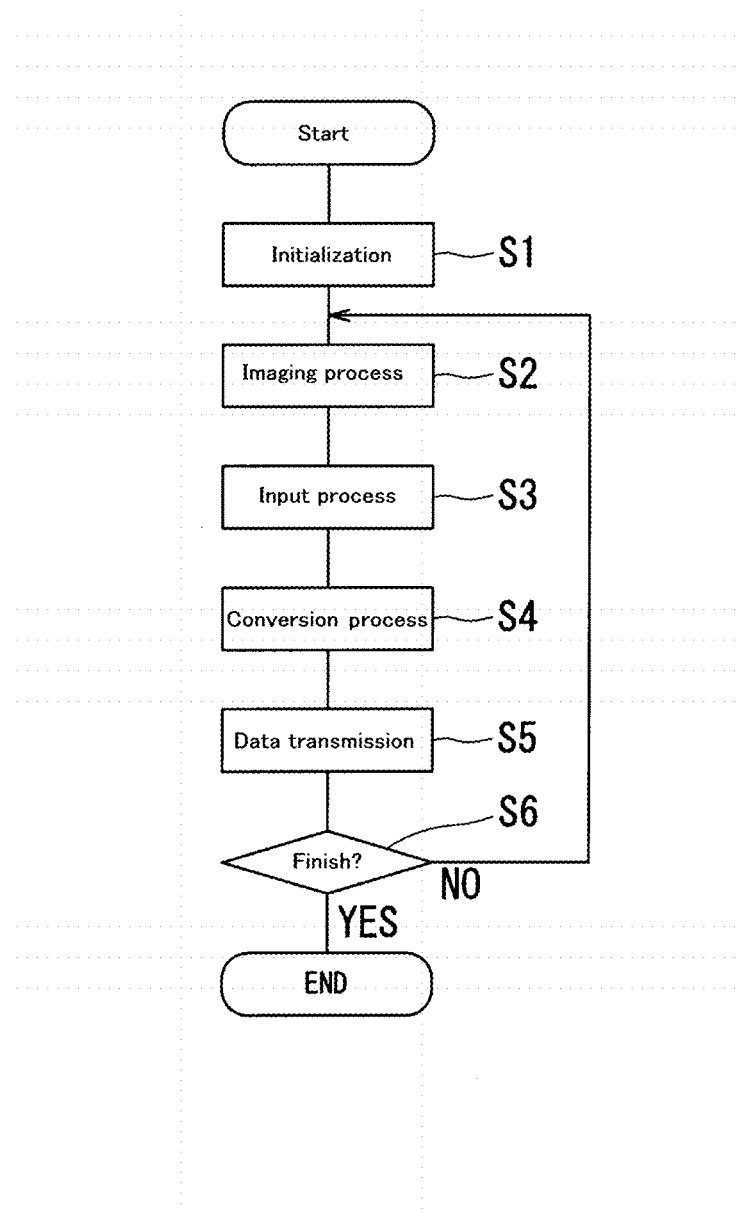
[Fig. 4]

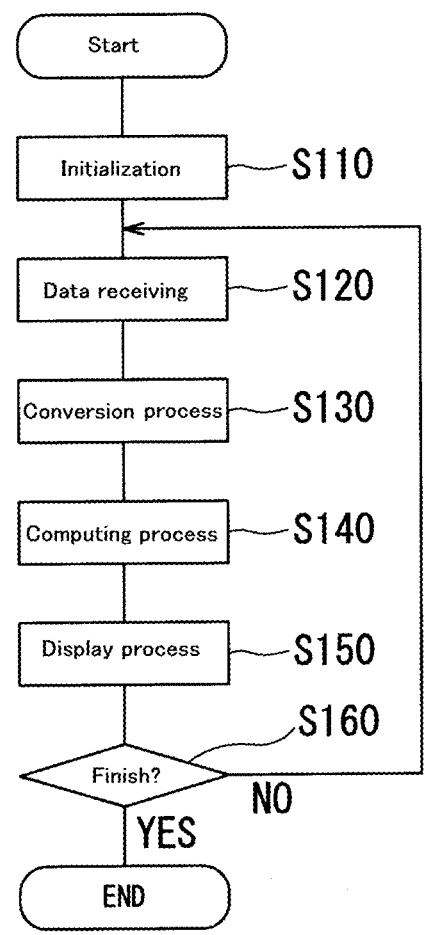
[Fig. 5]

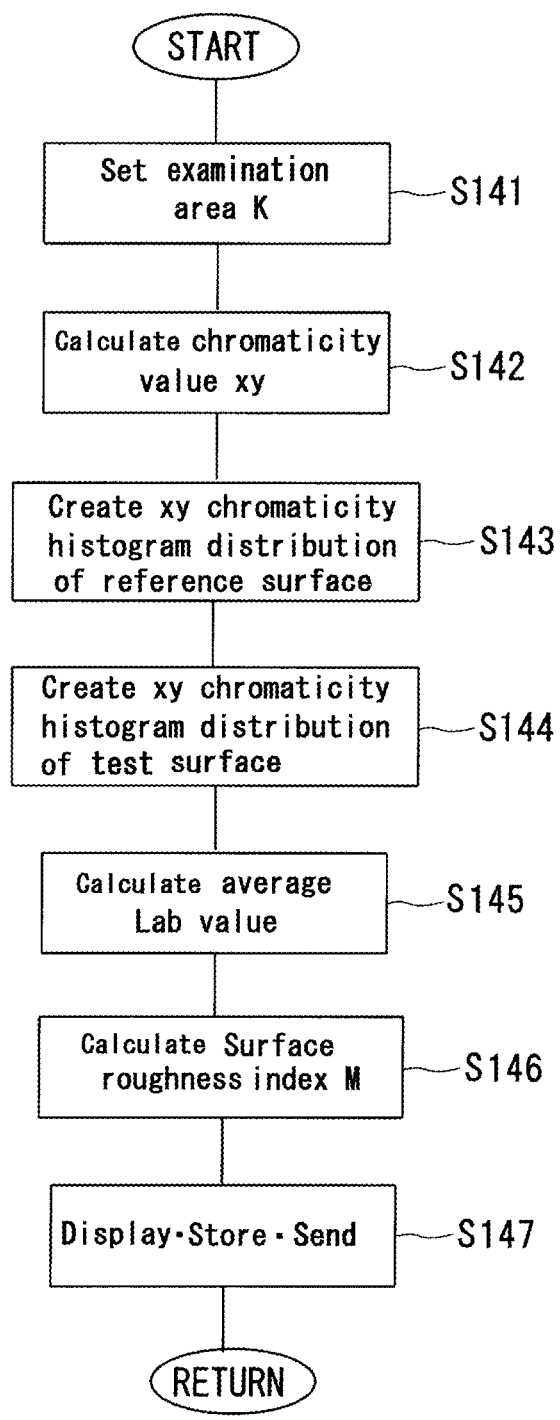
[Fig. 6]

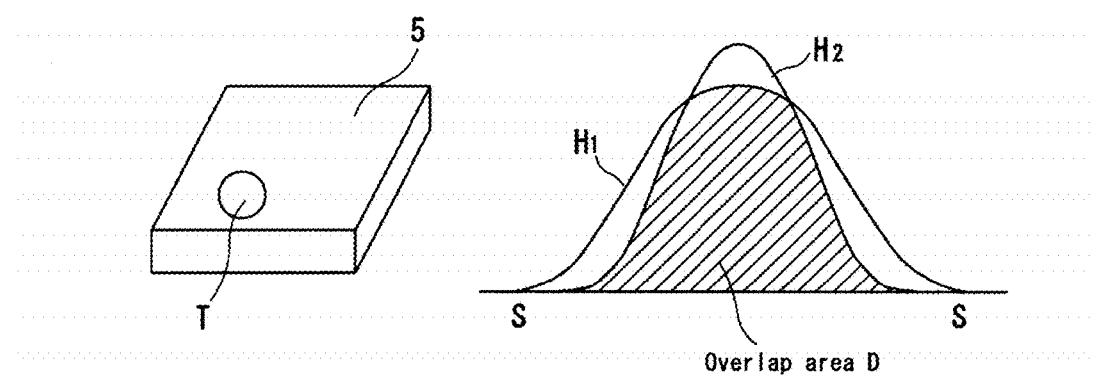
Fig. 7A
Fig. 7D
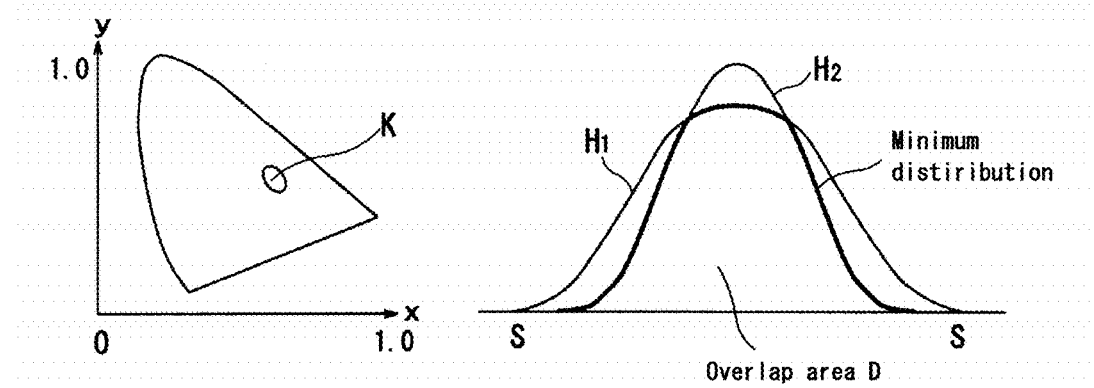
Fig. 7B
Fig. 7E
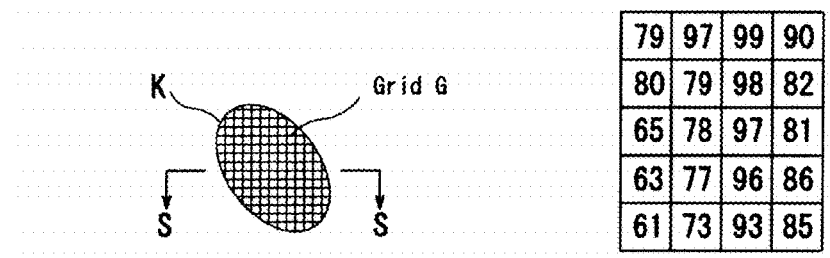
Fig. 7C
Fig. 7F

Integrating color information in measurement range
Distribution diagram on xy chromaticity diagram of color of 1 to 3

Three-dimensional diagram of integrated data
( Z axis corresponds to counting value )

SURFACE ROUGHNESS DETERMINATION APPARATUS USING A WHITE LIGHT SOURCE AND DETERMINATION METHOD

TECHNICAL FIELD

The present disclosure relates to a surface roughness determination apparatus using a white light source and a determination method, and more specifically relates to a determination apparatus configured to evaluate the matching degree of surface roughness and a corresponding method.

BACKGROUND

Various techniques have been proposed to polish the small irregularities on a surface, for example, a metal surface (http://www.chemicoat.co.jp/column/detail_6.html).

"Chemical polishing" is a polishing technique that soaks a metal in a polishing solution and causes the surface of the metal to be corroded by a chemical reaction of an acid or an alkali. The solution spreads into every corner of the metal and thereby enables even a microstructure which is not reachable by mechanical polishing to be processed. The chemical polishing technique is mainly suitable for polishing micro-components of complicated shapes and inner surfaces.

"Electrolytic polishing" is a polishing technique that soaks a metal in an electrolytic polishing solution and causes current to flow in the solution with the metal as the positive electrode. The metal is gradually dissolved to have the glossy or smoothened surface. This technique does not make an altered layer on the surface by processing and does not leave stain or burn. Along with the chemical polishing technique, the electrolytic polishing technique is accordingly used for precision components and the like that require a clean polishing technique.

"Mechanical polishing" is a polishing technique that uses a machine for polishing and includes various methods. The current mainstream is a rotary type that applies a polishing pad on a disk-shaped surface plate, drips a liquid polishing agent including a chemical component and fine particles on the polishing pad and rotates the surface plate to polish an object. Other polishing techniques include polishing with a horning machine to precisely polish an inner diameter of a metal object and buff polishing using a buff.

Satin finishing (http:/www.chemicoat.co.jp/knowledge/detail_169.html) is a surface treatment technique that make small irregularities on the surface of a metal and provides the rough surface finishing. Satin finishing includes glossy, semi-glossy and matte surface finishing. Satin finishing is used to provide the appropriate surface roughness and improve the appearance, and is additionally used to provide slip resistance against oily hands and pretreatment prior to coating or anode oxidation. A processing technique called "scraping" may be performed to provide small irregularities for the purpose of reducing the frictional resistance on the surface of a precision machine or the like.

Satin finishing techniques of a metal surface are mainly classified into mechanical methods and chemical methods. The mechanical methods include a wire-brushing method that polishes the surface using a wire brush, a sandblasting method that sprays fine particles onto the surface by means of the compressed air and a liquid horning method that sprays a processing solution including fine particles on a metal surface to be processed, in addition to the scraping method described above. The chemical satin finishing methods include a method employing chemical corrosion or galvanic corrosion such as etching and a surface treatment method using electroplating such as dispersal plating.

Roughness meters are generally used for measurement of the surface gloss and the surface roughness. The roughness meters include mechanical types and optical types, for example, using laser. The roughness meter provides a numerical indication of the irregularities in the unit of mm or in the unit of nm. Experienced engineers, however, often determine the surface roughness by observation of the surface gloss and glaze without using such measurement. The operations on the line proceed based on such experience. The following provides prior arts of the surface roughness measurement.

The disclosures of Patent Literatures 1 to 3 have been proposed to measure the surface roughness by profiling with a stylus or the like.

The disclosures of Patent Literatures 4 to 6 have been proposed to measure the surface roughness in a contactless manner with an imaging device.

The disclosures of Patent Literatures 7 to 10 have been proposed to measure the surface roughness in a contactless manner with laser beam.

CITATION LIST

Patent Literature

PTL 1: JP 2014-32177A
PTL 2: JP 2014-81324A
PTL 3: JP 2015-169641A
PTL 4: JP 2011-31370A
PTL 5 JP 4204879B
PTL 6: JP 2011-69688A
PTL 7: JP 2001-4351A
PTL 8: JP 2556556B
PTL 9: JP H06-307840A
PTL 10: JP 2015-143666A

SUMMARY

Technical Problem

The techniques of Patent Literatures 1 to 10, however, fail to determine the surface roughness indicating the degree of finishing, such as gloss, glaze or irregularities. The techniques of Patent Literatures 1 to 3 scan the surface using a contactor. The surface measurement by these techniques takes time and needs a large-scale device. The techniques of Patent Literatures 4 to 6 use visible light or the like and have insufficient accuracy. The techniques of Patent Literatures 7 to 10 scan the surface with a laser beam. Measurement of surface roughness by these techniques takes time.

The human eyes generally recognize the color of an object and the color of a light source in a balanced manner when observing the color of a glossy object. A totally reflected part has a high luminance, and the human eyes view the color strongly reflecting the light of the light source. A shaded part has, on the other hand, a low luminance and is highly affected by reflection of the target object. The human eyes feel additive color mixing for the middle between the highlight and the shade.

An object of, for example, embossed configuration does not have simple object color but structurally has total reflection. The prior art technique using an image, however, takes only an average color in only a limited area, while losing information of color expansion in, for example, $\Delta E$, $\Delta L$, $\Delta a$ and $\Delta b$. This results in losing the texture information of various colors and luminance values made by the complicated structure. There is also a variation in measured value at different measurement positions.

The surface finishing may be, for example, rough finishing or mirror finishing. Evaluation by a specialist vision is required to determine the degree of roughness in surface finishing.

The micro-surface finishing requires the roughness determination in micron-order, and the mirror surface finishing requires the roughness determination in nano-order. The human visual determination in both the micron-order and the nano-order takes time and is costly. Another problem is a difficulty in accurate determination. It is especially hard to accurately determine the surface roughness having the small irregularities of the low height. For example, a color shift is expected in determination of the surface roughness using the light having the wavelength of nano-level (for example, 700 nm) to micrometer-level. Although there is a demand for determination of the small roughness, such determination is not practically achieved.

When the surface of a metal is to be coated with a resin, coating should be performed after measurement of the surface to provide the optimum binding of the metal with the resin. It is, however, practically impossible to check such a small degree of roughness with a conventional roughness meter in the production line. This is a bottleneck in technical development. Scanning a surface with a conventional roughness meter takes a long measurement time. For example, repeating the line scan on the surface using AFM or laser to scan and measure the entire area takes a long measurement time and stops the production line. In many cases, products have gently curved surfaces, and industrial products have large areas to be measured. It is accordingly unpractical to measure the surface roughness of such products by the prior art techniques.

The present disclosure accordingly aims to irradiate the irregularities of a surface with light emitted from a light source, to measure a reflected light distribution from the surface by an XYZ-system imaging device, to observe the color and the roughness of the surface profile by scattering and diffraction of the light from the light source, and to quantify the degree of surface finishing based on the observed roughness in a state close to conditions of human visual determination.

The present disclosure also aims to allow for determination of the surface roughness having the small irregularities of the height in a nano-level to a micron-level, to shorten the measurement time and to ensure accurate roughness determination of a curved surface and a product of a large area.

Solution to Problem

The present disclosure provides a determination method using an XYZ-system imaging device that allows for determination extremely close to human visual determination. Since accurate values are obtainable two-dimensionally or three-dimensionally by the imaging device, this method quantifies the surface roughness, such as the irregularities of a test surface, by scattering and diffraction of illumination light.

The present disclosure focuses on the configuration that uses an XYZ-system imaging device to take an image of a surface irradiated with light from a light source and measures a reflected light distribution, observes the color and the surface roughness by scattering and diffraction of the light from the light source, and quantify the color of the surface and the surface roughness based on the observed roughness.

According to a first aspect of the present disclosure, there is provided a surface roughness determination apparatus using a white light source. The surface roughness determination apparatus using a white light source comprises an arithmetic processing unit configured to convert 3-band visual sensitivity images S1$i$, S2$i$ and S3$i$, which respectively have three spectral sensitivities (S1($\lambda$), S2($\lambda$) and S3($\lambda$)) subjected to linear transformation so as to be equivalent to a CIE XYZ color matching function and are obtained by an imaging device using the three spectral sensitivities (S1($\lambda$), S2($\lambda$) and S3($\lambda$)), into tristimulus values X, Y and Z in a CIE XYZ color system and perform arithmetic operations. The arithmetic processing unit comprises a color difference calculator configured to calculate a color difference $\Delta E$, a color space histogram distribution creator configured to divide an examination area of coordinates corresponding to a color space in the XYZ color system by grids and respectively integrate the numbers of pixels on a test surface and on a reference surface included in each of the grids, so as to create color space histogram distributions in the XYZ color system, a surface roughness index calculator configured to calculate a surface roughness index M indicating a difference between the two color space histogram distributions of the test surface and the reference surface with or without an offset correction, a surface roughness measurement data storage unit configured to store a measured surface roughness value Ra actually measured by a roughness meter, and a function setter configured to set at least one of a first calibration curve function indicating a correlation of the measured surface roughness value Ra to a surface roughness evaluation index Est, a second calibration curve function indicating a correlation of the measured surface roughness value Ra to the color difference $\Delta E$, a third calibration curve function indicating a correlation of the measured surface roughness value Ra to the surface roughness index M calculated without the offset correction and a fourth calibration curve function indicating a correlation of the measured surface roughness value Ra to the surface roughness index M calculate with the offset correction.

In the surface roughness determination apparatus using a white light source of the first aspect, the offset correction is performed by specifying the centers of the two color space histogram distributions of the test surface and the reference surface, and offsetting so as to bring one of the centers of the color space histogram distributions close to the other center of the color space histogram distribution. Further, in the surface roughness determination apparatus using a white light source of the first aspect, the surface roughness evaluation index Est is determined by specifying a first coefficient with regard to the surface roughness index and a second coefficient with regard to the color difference, such as to minimize an error between the surface roughness evaluation index Est and the measured surface roughness value Ra. For example, a preferable analysis technique employs multiple regression analysis to calculate the surface roughness evaluation index Est using the surface roughness index M and the color difference $\Delta E$.

According to a second aspect of the present disclosure, there is provided a surface roughness determination method using a white light source. The surface roughness determination method comprises an arithmetic processing step of converting 3-band visual sensitivity images S1$i$, S2$i$ and S3$i$, which respectively have three spectral sensitivities (S1($\lambda$), S2($\lambda$) and S3($\lambda$)) subjected to linear transformation so as to be equivalent to a CIE XYZ color matching function and are obtained by an imaging device using the three spectral sensitivities (S1(λ), S2(λ) and S3(λ)), into tristimulus values X, Y and Z in a CIE XYZ color system and performing arithmetic operations, a color difference calculating step of calculating a color difference ΔE, a color space histogram distribution creating step of dividing an examination area of coordinates corresponding to a color space in the XYZ color system by grids and respectively integrating the numbers of pixels on a test surface and on a reference surface included in each of the grids, so as to create color space histogram distributions in the XYZ color system, a surface roughness index calculating step of calculating a surface roughness index M indicating a difference between the two color space histogram distributions of the test surface and the reference surface with or without an offset correction, a surface roughness measurement data storing step of storing a measured surface roughness value Ra actually measured by a roughness meter and a function setting step of setting at least one of a first calibration curve function indicating a correlation of the measured surface roughness value Ra to a surface roughness evaluation index Est, a second calibration curve function indicating a correlation of the measured surface roughness value Ra to the color difference ΔE, a third calibration curve function indicating a correlation of the measured surface roughness value Ra to the surface roughness index M calculated without the offset correction and a fourth calibration curve function indicating a correlation of the measured surface roughness value Ra to the surface roughness index M calculated with the offset correction.

In the surface roughness determination method of the second aspect, the offset correction is performed by specifying the centers of the two color space histogram distributions of the test surface and the reference surface, and offsetting so as to bring one of the centers of the color space histogram distributions close to the other center of the color space histogram distribution. Further, in the surface roughness determination method of the second aspect, the surface roughness evaluation index Est is determined by specifying a first coefficient with regard to the surface roughness index and a second coefficient with regard to the color difference, such as to minimize an error between the surface roughness evaluation index Est and the measured surface roughness value Ra.

The "imaging device" takes images of a reference surface and a test surface in three different channels with three spectral sensitivities (S1(λ), S2(λ) and S3(λ)). The imaging device may employ any means for imaging, for example, optical filters, dichroic mirrors or a dichroic prism set to provide these spectral sensitivities.

The spectral sensitivities (S1(λ), S2(λ) and S3(λ)) of the "imaging device" are obtained by equivalent transformation from CIE XYZ spectral characteristics under the conditions that the respective spectral sensitivity curves do not take negative values, are bell-shaped curves with single peaks, have equal peak values, and have smallest possible overlaps. The spectral characteristic S1 curve has a peak wavelength of 582 nm, a half width of 523 to 629 nm and a 1/10 width of 491 to 663 nm. The spectral characteristic S2 curve has a peak wavelength of 543 nm, a half width of 506 to 589 nm and a 1/10 width of 464 to 632 nm. The spectral characteristic S3 curve has a peak wavelength of 446 nm, a half width of 423 to 478 nm and a 1/10 width of 409 to 508 nm.

The "surface" may be, for example, a resin surface, a metal surface or a ceramic surface. The resin surface includes, for example, an embossed surface. The metal surface includes, for example, a surface of a cutting tool, a surface of a metal mold and a surface of plating. The surface includes a curved surface and a surface of a complicated shape, in addition to a flat surface.

The "evaluation" means evaluation of the surface roughness. The "index" may be any of various configurations including two-dimensional and three-dimensional indications, and is, for example, an index number, a graph, a pictorial diagram or a combination thereof.

The "roughness meter" may be, for example, an atomic force microscope (AFM), a laser roughness meter (for example, in the case of measurement in nanometer-order), or a contact mechanical roughness meter (for example, in the case of measurement in micron-order). Any of these measurement machines is used to obtain actually measured values. The AFM (atomic force microscope) roughness meters include contactless types and contact types. The AFM roughness meter obtains an image by detecting the force acting between atoms of a sample and a probe and has high accuracy. An example is a scanning probe microscope (SPM) that measures the roughness in micron-order level or in nano-order level. The measurement system may be selected appropriately according to the roughness level of an object to be measured.

Each of the "first calibration curve function, second calibration curve function and third calibration curve function" may be either a linear function or a curved function.

It is preferable to set one calibration curve with regard to one reference surface. This is because the standard of the calibration curve in the mechanical system, in the laser system or the like depends on the degree of irregularities of the reference surface.

The XYZ color system means the XYZ color system in the broad sense including other CIE color systems in the claims and means the XYZ color system in the narrow sense in the description other than the claims. The XYZ color system in the narrow sense is determined such that no negative value appears by simple linear transformation of an RGB color system, is used as the basis of other CIE color systems, for example, CIE Yxy, XYZ, Lab and Luv color systems, and is a concept including a two-dimensional chromaticity diagram or a three-dimensional color space. The XYZ color system in the broad sense includes the XYZ color system in the narrow sense and other CIE color systems developed from the XYZ color system in the narrow sense.

The XYZ color system in the narrow sense was provided along with the RGB color system by CIE in 1931, such that no negative value appears by simple linear transformation of the RGB color system.

The xyY color system (also called Yxy color system) is determined from the XYZ color system to express the absolute color tone, since the relationship of the numerical value to the color is not readily understandable in the XYZ color system.

The Luv color system is one of uniform color spaces determined by CIE in 1976. The CIE Luv color system improves the uniformity of the wavelength interval in the xy chromaticity diagram in the XYZ color system, based on the wavelength of light and is specified in JIS Z8518 in Japan.

The Lab color system is a CIE Lab system derived from the XYZ color system to measure a color difference due to the variation in perception and the difference of the device and is specified in JIS Z8729 in Japan. The calibration curve in the Lab color system may be effective for evaluation of the roughness in nano-order.

The XYZ color system in the broad sense includes color spaces defined by two-dimensional coordinates and color spaces defined by three-dimensional coordinates. Typical examples of the color space include an xy color space, an XYZ color space and an Lab color space. Examples of the two-dimensional color space include a Yxy color space and an Luv color space. Examples of the chromaticity diagram in a two-dimensional plane include an xy chromaticity diagram (xy chromaticity values (plane) normalized in a Yxy color space), a uv chromaticity diagram and a u'v' chromaticity diagram. This corresponds to, for example, an xy chromaticity histogram distribution or an Luv chromaticity histogram distribution expressed as the density of pixels in the two-dimensional chromaticity diagram on the plane. Examples of the three-dimensional color space include an XYZ color space and an Lab color space. This corresponds to, for example, an XYZ color space histogram distribution or an Lab color space histogram distribution expressed as the density of pixels on the three-dimensional color space.

The xy chromaticity diagram, the uv chromaticity diagram and the u'v' chromaticity diagram two-dimensionally separate the surface roughness from the color, whereas the XYZ color space, the Lab color space and the like separate the surface roughness from the color on the three-dimensional color space. Accordingly, the XYZ color space histogram, the Lab color space histogram, and the like are defined distinctively from the xy chromaticity histogram.

The "XYZ color space histogram" and the "Lab color space histogram" are different from each other. A surface roughness index in the Lab color space is calculated from Lab color space data converted from XYZ color space data.

Any of various offsetting techniques may be employed to bring one histogram distribution close to the other histogram distribution for an offset, as long as such an offset provides an appropriate index; for example, a technique of causing the center of one histogram distribution to match with the center of the other histogram distribution, a technique of bringing the respective centers of histogram distributions close to each other in a predetermined range, a technique of moving one histogram distribution in parallel to a coordinate axis to be close to the other histogram distribution, or a technique of linearly moving one center to be close to the other center.

The index is not limited to a two-dimensional form or a three-dimensional form but may be any of various forms, such as an index number, a graph, a graphic or any combination thereof.

Advantageous Effects

The present disclosure uses the XYZ imaging device to quantify the surface roughness and advantageously enables determination extremely close to the human visual determination to be performed accurately and efficiently. The present disclosure also shortens the evaluation time of the surface roughness and allows for evaluation of the roughness of a curved surface.

The present disclosure advantageously enables the roughness in nano-order or in micron-order to be evaluated accurately and efficiently.

BRIEF DESCRIPTION OF DRAWINGS

FIG. 3A is a diagram illustrating a method using dichroic mirrors; FIG. 3B is a diagram illustrating a method using a filter turret; and FIG. 3C is a diagram illustrating a method using optical filters 22a, 22b and 22c microscopically applied to an imaging element 23;

FIG. 4 is a flowchart in the two-dimensional colorimeter 2 according to Embodiment 1 of the present disclosure;

FIG. 5 is a flowchart in an arithmetic processing unit 3 according to Embodiment 1 of the present disclosure;

FIG. 6 is a sub-chart in the arithmetic processing unit 3 according to Embodiment 1 of the present disclosure;

FIG. 7A is a diagram illustrating an examination area T in the surface roughness determination apparatus 1 according to Embodiment 1 of the present disclosure; FIG. 7B is an xy chromaticity diagram illustrating an examination area K corresponding to the examination area T; FIG. 7C is a diagram illustrating the examination area K divided by grids G; FIG. 7D is a diagram illustrating an overlap of chromaticity on the two-dimensional xy chromaticity diagram; FIG. 7E is a diagram illustrating a minimum distribution; and FIG. 7F is a diagram showing one example of an xy chromaticity histogram distribution;

DESCRIPTION OF EMBODIMENTS

A surface roughness determination apparatus 1 using a white light source according to Embodiment 1 of the present disclosure is described with reference to FIGS. 1 to 12.

The surface roughness determination apparatus 1 includes an arithmetic processing unit 3 configured to convert 3-band visual sensitivity images S1$i$, S2$i$ and S3$i$, which respectively have three spectral sensitivities (S1($\lambda$), S2($\lambda$) and S3($\lambda$)) subjected to linear transformation equivalent to a CIE XYZ color matching function and are obtained from a surface 5 by a two-dimensional colorimeter 2 using the three spectral sensitivities (S1($\lambda$), S2($\lambda$) and S3($\lambda$)), into tristimulus values X, Y and Z in a CIE XYZ color system and perform arithmetic operations. This arithmetic processing unit 3 includes a color difference calculator configured to calculate a color difference ΔE; a color space histogram distribution creator configured to divide an examination area of coordinates corresponding to a color space in the XYZ color system by grids G and respectively integrate the numbers of pixels on a test surface and on a reference surface included in each of the grids G, so as to create color space histogram distributions in the XYZ color system; a surface roughness index calculator configured to calculate a surface roughness index M indicating a difference between the two color space histogram distributions of the test surface and the reference surface; a surface roughness measurement data storage unit configured to store a measured surface roughness value Ra actually measured by a roughness meter; and a function setter configured to set at least one of a first calibration curve function L1 indicating a correlation of the measured surface roughness value Ra to a surface roughness evaluation index Est, a second calibration curve function L2 indicating a correlation of the measured surface roughness value Ra to the color difference ΔE and a third calibration curve function L3 indicating a correlation of the measured surface roughness value Ra to the surface roughness index M. The surface roughness evaluation index Est is determined by specifying a first coefficient a with regard to the surface roughness index M and a second coefficient b with regard to the color difference ΔE, such as to minimize an error Error between the surface roughness evaluation index Est and the measured surface roughness value Ra.

Figure 2:
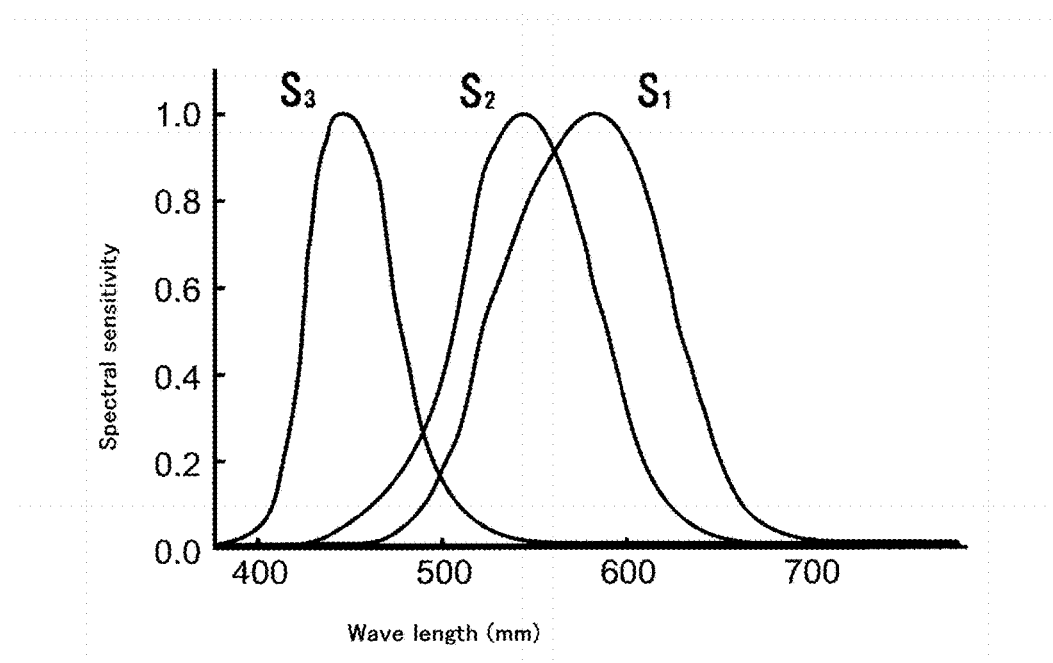
FIG. 2 is a diagram showing functions of spectral sensitivities of a two-dimensional colorimeter 2 in an XYZ color system according to Embodiment 1 of the present disclosure.
Figure 3:
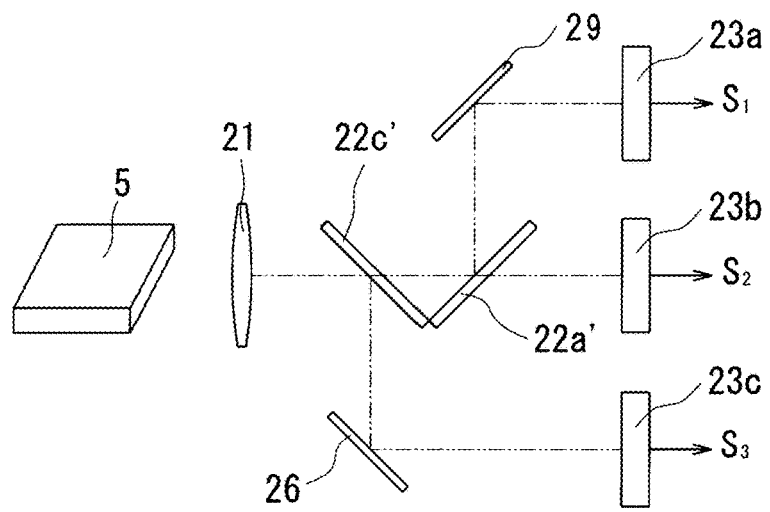
FIGS. 3A, 3B, and 3C are diagrams illustrating concrete methods of obtaining image information with three spectral sensitivities ($S1(\lambda)$, $S2(\lambda)$ and $S3(\lambda)$) according to Embodiment 1 of the present disclosure.
Figure 3:
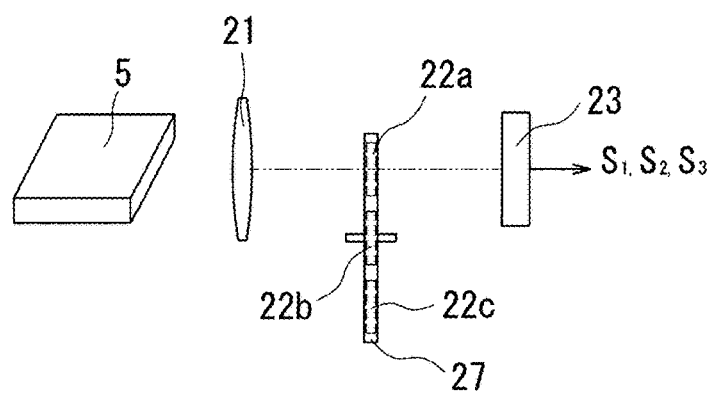
Figure 3:
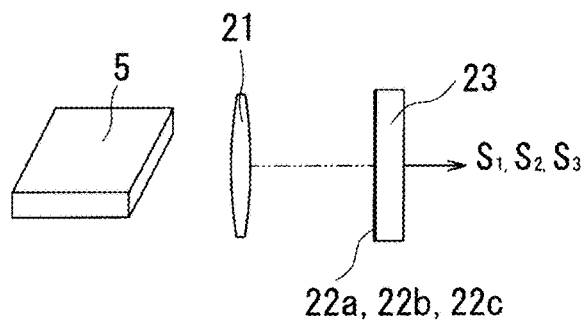
Figure 8:
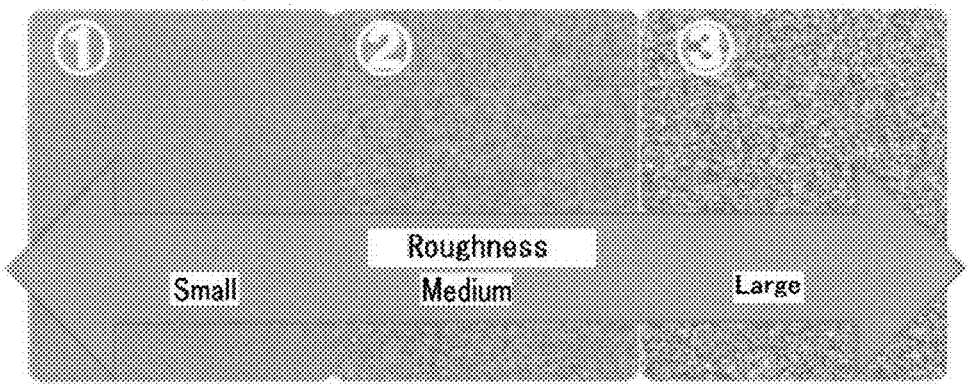
FIG. 8A is a diagram illustrating a variation in surface roughness.
FIG. 8B is a diagram illustrating xy chromaticity histogram distributions.
FIG. 8C is three-dimensional image diagrams illustrating xy chromaticity histogram distributions.
Figure 8:
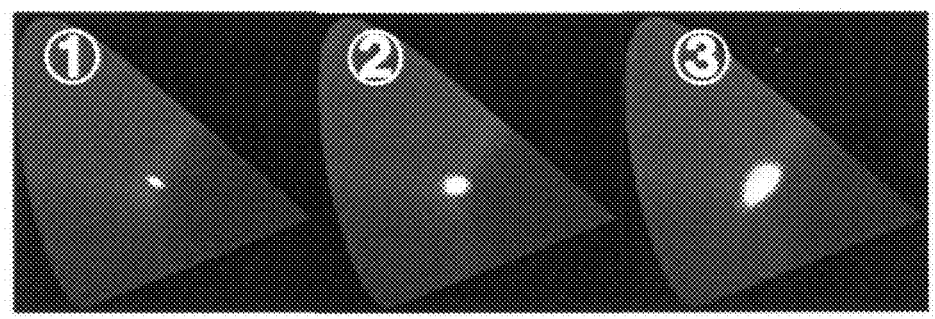
Figure 8:
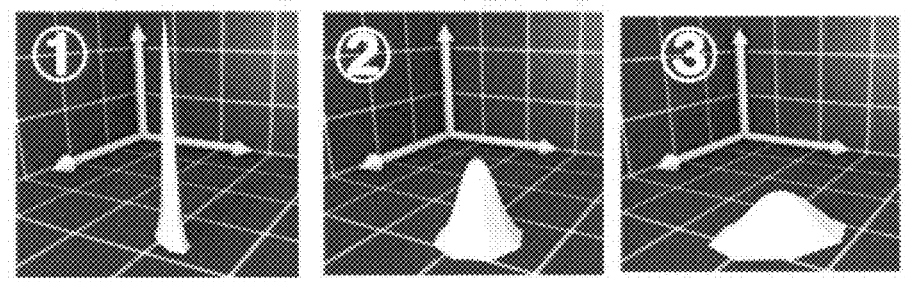

The spectral sensitivities (S1($\lambda$), S2($\lambda$) and S3($\lambda$)) of the two-dimensional colorimeter 2 satisfy router conditions and are obtained by equivalent transformation from an XYZ color-matching function under the conditions that the respective spectral sensitivity curves do not take negative values, are bell-shaped curves with single peaks, have equal peak values, and have smallest possible overlaps as shown in FIG. 2. The spectral sensitivities (S1($\lambda$), S2($\lambda$) and S3($\lambda$)) specifically have the following characteristics:

|    | Peak Wavelength | Half Width | 1/10 Width |
|----|-----------------|------------|------------|
| S1 | 582 nm          | 523-629 nm | 491-663 nm |
| S2 | 543 nm          | 506-589 nm | 464-632 nm |
| S3 | 446 nm          | 423-478 nm | 409-508 nm |

The peak wavelength of the spectral characteristic curve S1 may be expressed as 580±4 nm; the peak wavelength of the spectral characteristic curve S2 may be expressed as 543±3 nm; and the peak wavelength of the spectral characteristic curve S3 may be expressed as 446±7 nm.

The three spectral sensitivities (S1($\lambda$), S2($\lambda$) and S3($\lambda$)) are obtained by using Mathematical Expression 1 given below. Refer to JP 2005-257827A for the further details of the spectral characteristics:

$$\begin{bmatrix} S_1(\lambda) \\ S_2(\lambda) \\ S_3(\lambda) \end{bmatrix} = \begin{bmatrix} 0.51151 & 0.60975 & -0.10930 \\ -0.38668 & 1.16031 & 0.07538 \\ 0.0 & 0.0 & 0.56086 \end{bmatrix} \begin{bmatrix} \bar{x}(\lambda) \\ \bar{y}(\lambda) \\ \bar{z}(\lambda) \end{bmatrix} \quad \text{[Math. 1]}$$

The two-dimensional colorimeter 2 used may be, for example, a two-dimensional colorimeter RC-500 manufactured by PaPaLab Co., Ltd. having the following specifications: effective frequency value of approximately 5 million pixels; effective area of 9.93 mm×8.7 mm; image size of 3.45 μm×3.45 μm; video output of 12 bits, GigE as camera interface; number of frames (at the time of focus adjustment) of 3 to 7 frames/sec; shutter speed of 1/15,600 sec to 1/15 sec; integration time of up to 3 seconds; S/N ratio of not lower than 60 dB; F mount as the lens mount; operation temperature of 0° C. to 40° C.; and operation humidity of 20% to 80%.

Figure 1:
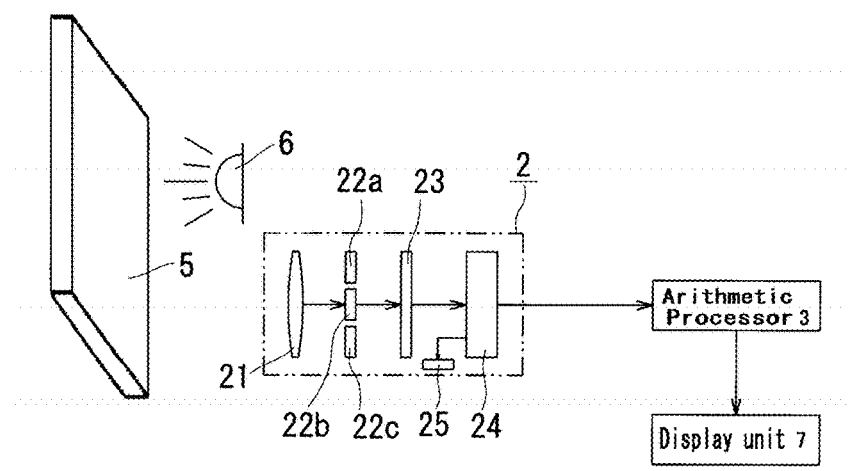
FIG. 1 is a block diagram illustrating a surface roughness determination apparatus 1 using a white light source according to Embodiment 1 of the present disclosure.

As shown in FIG. 1, the two-dimensional colorimeter 2 includes an imaging lens 21, three optical filters 22a, 22b and 22c placed behind this imaging lens 21, and an imaging element 23 (for example, CCD or CMOS) placed behind the optical filters 22a, 22b and 22c. The three spectral sensitivities ($S1(\lambda)$, $S2(\lambda)$ and $S3(\lambda)$) of the two-dimensional colorimeter 2 are given as the products of the spectral transmittances of the optical filters 22a, 22b and 22c and the spectral sensitivity of the imaging element 23. The positional relationship between the optical filters 22a, 22b and 22c and the imaging element 23 shown in FIG. 1 is only illustrative. The following describes concrete methods of obtaining the 3-band visual sensitivity images S1i, S2i and S3i with the three spectral sensitivities ($S1(\lambda)$, $S2(\lambda)$ and $S3(\lambda)$). This Embodiment 1 may employ any of these methods or may employ another suitable method. A reference numeral 24 corresponds to an arithmetic unit and a reference numeral 25 corresponds to a display unit.

FIG. 3A shows a method using dichroic mirrors. This method uses a dichroic mirror 22c' to reflect the light of a specific wavelength, uses another dichroic mirror 22a' to reflect and disperse the light of another specific wavelength out of the transmitted remaining light, and reads the 3-band visual sensitivity images from three imaging elements 23a, 23b and 23c placed parallel to one another. In this method, the dichroic mirror 22a' corresponds to the optical filters 22a and 22b, and the dichroic mirror 22c' corresponds to the optical filter 22c. The dichroic mirror 22c' reflects the light of the spectral sensitivity S3 out of the light entering from the imaging lens 21, while causing the remaining light to be transmitted. The light reflected by the dichroic mirror 22c' is further reflected by a reflector 26, and the visual sensitivity image S3i is obtained by the imaging element 23c. The dichroic mirror 22a' reflects the light of the spectral sensitivity S1 out of the light transmitted through the dichroic mirror 22c', while causing the remaining light of the spectral sensitivity S2 to be transmitted. The respective rights are imaged by the imaging elements 23a and 23b, and the visual sensitivity images S1i and S2i are obtained. The light transmitted through the dichroic mirror 22a' is imaged by the imaging element 23b, and the spectral sensitivity S2 is obtained. The light reflected by the dichroic mirror 22a' is reflected by the mirror 29, and the spectral sensitivity S1 is obtained by the imaging element 23a. A modification may use a dichroic prism having similar characteristics in place of the dichroic mirrors to disperse the incident light into three spectral lights and may use imaging elements 23a, 23b and 23c adhering at positions of transmission of the respective spectral lights.

FIG. 3B shows a method using a filter turret 27. The filter turret 27 has a rotating axis that is arranged in the same direction as the direction of the incident light from an imaging lens 21, and is provided with optical filters 22a, 22b and 22c that are mechanically rotated. The sequentially transmitted lights are imaged by an imaging element 23, and the 3-band visual sensitivity images S1i, S2i and S3i are obtained.

FIG. 3C shows a method using optical filters 22a, 22b and 22c that are microscopically applied to an imaging element 23. The optical filters 22a, 22b and 22c placed on the imaging element 23 are provided in a Bayer array. In this array, the optical filter 22b is arranged in half an area on the imaging element 23 that is divided in a grid-like pattern, and the optical filter 22a and the optical filter 22c are arranged evenly in the remaining half area. Accordingly, the arrangement of optical filter 22a:optical filter 22b:optical filter 22c is equal to 1:2:1. The arrangement of the optical filters 22a, 22b and 22c may, however, be other than the Bayer array in Embodiment 1. Each of the optical filters 22a, 22b and 22c is very small and is applied on the imaging element 23 by printing. The present disclosure is, however, not characterized by this array but is characterized by the configuration that the filters having the characteristics of the spectral sensitivities ($S1(\lambda)$, $S2(\lambda)$ and $S3(\lambda)$) are applied to the imaging element.

The two-dimensional colorimeter 2 sends image information obtained with the spectral sensitivities ($S1(\lambda)$, $S2(\lambda)$ and $S3(\lambda)$) to the arithmetic processing unit 3. The arithmetic processing unit 3 converts the image information into tristimulus values X, Y and Z in the XYZ color system and performs an arithmetic operation by a conversion process with regard to image data having the obtained tristimulus values X, Y and Z. A display device 7 is provided to display a visualized image.

The arithmetic processing unit 3 computes and visualizes the roughness, the color difference and the like at any arbitrary position of the image obtained by the two-dimensional colorimeter 2. The surface 5 is illuminated from directly above or obliquely downward, and xy, XYZ or Lab chromaticity distribution data are compared and indexed.

The two-dimensional colorimeter 2 generally takes an image of the surface 5 at one position and may be moved to take an image at another angle as needed basis. The surface 5 may be imaged at three different positions, for example, front, 45 degrees left and 45 degrees right (or any appropriate number of different positions).

A lighting unit 6 employs a xenon lamp (artificial sunlight) as the light source. The lighting unit 6 includes a Fresnel lens assembly in addition to the xenon lamp. The xenon lamp is arranged to illuminate the surface 5 uniformly obliquely downward. The xenon lamp may be replaced by an LED artificial sunlamp.

The display device 7 is connected with the arithmetic processing unit 3 and is configured to receive an image signal processed by the arithmetic processing unit 3 and display an image on the screen. The arithmetic processing unit 3 or the display device 7 appropriately includes an input unit (not shown) and the like. The input unit may be, for example, a keyboard, a mouse or a touch panel provided on a display.

The following describes the operations of the surface roughness determination apparatus 1 for the surface 5 with reference to a concrete example. As shown in FIG. 1, the surface roughness determination apparatus 1 for the surface 5 is operated by connecting the two-dimensional colorimeter 2, the arithmetic processing unit 3 and the display device 7 with each other. The connection system may be wired or wireless. A flowchart in the surface roughness determination apparatus 1 and a flowchart in the arithmetic processing unit 3 and the display device 7 are respectively shown in FIG. 4 and in FIG. 5.

As shown in FIG. 4, when the two-dimensional colorimeter 2 is powered on, the two-dimensional colorimeter 2 is first initialized (initialization S1). The two-dimensional colorimeter 2 subsequently takes images of the surface 5 (imaging process S2) and inputs the obtained 3-band visual sensitivity images S1$i$, S2$i$ and S3$i$ from the imaging element 23 (input process S3). The arithmetic processing unit 3 then converts the input 3-band visual sensitivity images S1$i$, S2$i$ and S3$i$ into tristimulus values X, Y and Z (conversion process S4) and sends 3-band visual sensitivity images S1$i$, S2$i$ and S3$i$ to the display device 7 (data sending S5). When the image is a moving image, the series of processing from the imaging process S2 to the data sending S5 is performed continuously (S6). The image is displayed on the display device 7.

Mathematical Expressions 2 and 3 show conversion equations from the tristimulus values X, Y and Z into a Y'xy color system. A luminance meter (not shown) is used along with the two-dimensional colorimeter 2, and the value Y is corrected to Y' with a value (nt) of the luminance meter. The conversion equations in the color space are generally used, and the other detailed equations are omitted herein.

The XYZ color system is the basis of the respective color systems as the CIE standard color system. The XYZ color system is developed based on the principle of additive color mixing of three primary colors of light (R=red, G=green and B=blue) and expresses the color by three values Yxy by using a chromaticity diagram. Y denotes a reflectance and corresponds to the lightness, and xy denote chromaticities.

$$x = \frac{X}{X+Y+Z} \quad [\text{Math. 2}]$$

$$y = \frac{Y}{X+Y+Z} \quad [\text{Math. 3}]$$

The imaging process S2 is a process of imaging the surface 5 by the two-dimensional colorimeter 2 having the three spectral sensitivities (S1($\lambda$), S2($\lambda$) and S3($\lambda$)) (as shown in FIG. 1 and FIG. 4). The spectral sensitivities (S1($\lambda$), S2($\lambda$) and S3($\lambda$)) are given according to Mathematical Expression 1 above. The input process S3 is continuously performed simultaneously with imaging with the imaging lens 21, the optical filters 22$a$, 22$b$ and 22$c$ and the imaging element 23.

The input image data are values with the spectral sensitivities (S1($\lambda$), S2($\lambda$) and S3($\lambda$)). The conversion process S4 in the arithmetic processing unit 3 connected with the two-dimensional colorimeter 2 converts the image data of the taken image into tristimulus values X, Y and Z. This conversion is performed according to Mathematical Expression 1. Accordingly, the tristimulus values X, Y and Z are obtained by multiplying the image data by an inverse matrix of the coefficients in Mathematical Expression 1. The values with the spectral sensitivities (S1($\lambda$), S2($\lambda$) and S3($\lambda$)) are sent from the two-dimensional colorimeter 2 to the arithmetic processing unit 3.

As shown in FIG. 5, when the arithmetic processing unit 3 is powered on, the arithmetic processing unit 3 is first initialized (initialization S110). In the state that the display device 7 is connected with the two-dimensional colorimeter 2, the arithmetic processing unit 3 receives the 3-band visual sensitivity images S1$i$, S2$i$ and S3$i$ sent from the two-dimensional colorimeter 2 (data receiving S120). The arithmetic processing unit 3 subsequently converts the 3-band visual sensitivity images S1$i$, S2$i$ and S3$i$ into tristimulus values X, Y and Z and computes and visualizes Lab average values and xy surface roughness indexes M of the taken images of a reference surface and a test surface (S130). The color information may be converted into RGB data or the like as needed for display on the display device 7 (S140). The obtained data are sent to the display device 7 (display process S150). After data receiving S120 from the two-dimensional colorimeter 2, the series of processing from the conversion process S130 to the display process S150 is performed sequentially (S160).

The display process S150 described above is a process of displaying the visualized surface roughness index M on the display device 7. The processing flow is then returned.

The following describes a sub flowchart of S140 with reference to FIG. 6. A first image (image B) of a reference surface and a second image (image A) of a test surface to be compared are taken, and surface roughness indexes M are sequentially computed as described below. The similarity of the surface roughness is determined using the surface roughness indexes M of the separated surface roughness.

An examination area K (shown in FIG. 7B) corresponding to an area T to be examined (shown in FIG. 7A) is set with regard to the taken images A and B (S141). The dimensions and the location of the examination area K may be set freely.

Chromaticities xy are subsequently calculated (S142).

An xy chromaticity histogram distribution is created with regard to the examination area K of the reference surface cut from the taken image B of the reference surface (S143).

The xy chromaticity histogram distribution is a three-dimensional histogram showing the integrated number of pixels included in each of the unit grids G described above.

FIG. 7F two-dimensionally shows a color distribution of the object for comparison at positions of xy coordinates. The examination area K is divided by the grids G as shown in FIG. 7C, and a histogram distribution is created by integrating the number of pixels having the xy values in each grid as the z axis. The xy coordinates are divided by grids of a specific width, for example, by plane grids of a width ¹⁄₁₀₀₀ (divided by 1000 lines). The examination area K is scanned from one end to the other end, and the number of pixels included in each area divided by the grids G is integrated in the z direction. Calculation in only a specific range of the xy coordinates in the examination area K shortens the calculation time. The finer division of the grids increases the accuracy but also increases the calculation time. The size of the grid is thus determined appropriately.

Like S143, an xy chromaticity histogram distribution is created with regard to the image A of the test surface (S144). The xy chromaticity histogram distribution shows the xy chromaticities as the xy axes and the integrated number of pixels as the z axis.

L, a and b values on the axis a, the axis b and the axis L are independently summed up with regard to all the pixels included in the examination area K. An average L value, an average a value and an average b value in the Lab chromaticity distribution are calculated by dividing the respective sums of the L value, the a value and the b value by the number of pixels. The color difference ΔE is also calculated according to Mathematical Expression 4 (S145).

$$\Delta E = \sqrt{\Delta L^2 + \Delta a^2 + \Delta b^2} \quad \text{[Math. 4]}$$

Converted L, a and b values in the Lab space are calculated according to Mathematical Expression 5 given below. The Lab color space is a type of complementary color space and has a dimension L indicating the lightness and complementary color dimensions A and B. The Lab color space is based on non-linear compression of the coordinates in the CIE XYZ color space. The X, Y and Z values prior to normalization are converted into the L, a and b values by Mathematical Expression 5. The distribution in the Lab color space additionally has the lightness direction relative to the distribution on the XYZ color space.

$$f(t) = \begin{cases} t^{1/3} & \text{When } t > (6/29)^3 = \\ & 0.008856\ldots \\ [(29/3)^3 t + 16]/116 & \text{Otherwise} \end{cases} \quad \text{[Math. 5]}$$

$$L^* = 116 f(Y/Y_n) - 16$$

$$a^* = 500[f(X/X_n) - f(Y/Y_n)]$$

$$b^* = 200[f(Y/Y_n) - f(Z/Z_n)]$$

In Mathematical Expression 5, the X, Y and Z values in parentheses of the function f are respectively divided by coordinates Xn, Yn and Zn of a white point, with a view to adjusting the maximum value to 1.

Differences of the average values between the reference surface and the test surface are computed and are used as the criteria for determination of the color difference.

The surface roughness index M is calculated (S146). This simply separates and quantifies the degree of roughness. The roughness is calculated in the two-dimensional space of the xy chromaticity distribution, and the difference in roughness is determinable separately from the color. This securely enables the color and the surface roughness to be detected separately.

The surface roughness index M is calculated by an expression given below. The xy chromaticity histogram distribution shows the integrated number of pixels. FIG. 7D shows the overlap area D, and FIG. 7E shows a minimum distribution:

surface roughness index M=integrated number of pixels included in the overlap area D/total number of pixels included in the examination area K×100(%)

xy chromaticity histograms of the reference surface and the test surface are calculated on the two-dimensional space. Minimum values at the same positions in the arrays indicate an overlap frequency. The surface roughness index M is accordingly calculated by dividing the overlap frequency by the total number of pixels in the histogram.

FIG. 7D and FIG. 7E-show one sectional view taken along an S-S section in FIG. 7C There is an overlap when the xy coordinates are viewed from the same line. These sectional views are not shown three-dimensionally but are shown as planar diagrams for the purpose of convenience. The histogram is given as a fine step-like distribution. An integrated number H1 and an integrated number H2 shown in FIG. 7D respectively correspond to the image A and the image B. Comparison between the two histogram distributions provides an overlap area D.

As shown in FIG. 7E when H1(x1, y1) shows an integrated number in the xy chromaticity histogram of the test surface, and H2(x2, y2) shows an integrated number in the xy chromaticity histogram of the reference surface, H1 is larger than H2 in a left side area of the overlap, H1 is smaller than H2 in the center of the overlap, and H1 is larger than H2 in a right side area of the overlap. When the smaller integrated number (pixel frequency) between H1 and H2 is taken, H2 is taken in the left side area and in the right side area and H1 is taken in the center area. This specifies a minimum distribution that is a step-like histogram curve. A two-dimensional or three-dimensional ratio of the overlap area D to the total area is calculated by using the minimum distribution.

The smaller integrated number is specified in this minimum distribution. Summation of the smaller integrated numbers between H1 and H2 calculates the integrated number in the overlap area D, and the ratio to the total number of pixels is specified. The total number of pixels in the examination area K is fixed, and the test surface and the reference surface have the same total number of pixels. The ratio may be calculated by three-dimensional integration with regard to all the grids G. For example, as shown in FIG. 7C, the examination area K may be cut along the S-S axis, and the distributions of the integrated numbers of pixels H1 and H2 are two-dimensionally integrated by changing x from one end to the other end at a predetermined value y. FIG. 7F is one example of an xy chromaticity histogram distribution. Results showing zero as the number of pixels and indicating no distribution in the examination area K are excluded from the calculation.

A display and storage process and a sending process are then performed (S147), and the processing flow is returned.

For example, it is assumed that the number of pixels included in the examination area K is 100 pixels in length× 100 pixels in width=10,000 pixels. The corresponding examination area K is cut out from each image, so that the total number of pixels is 10,000 pixels with regard to both the image A and the image B. The number of pixels included in the overlap area D is integrated from the xy chromaticity histogram. When the number of pixels in the overlap area D is 5,000, the surface roughness index M is 50%. A decrease of the surface roughness index M from 100% indicates an increase in difference of surface roughness. Complete matching between distributions of xy values indicates the surface roughness index M of 100%. A surface having the surface roughness index M equal to or higher than a predetermined value is thus determined as an adequate surface with regard to the surface roughness.

Color information obtained primarily from the image is based on three spectral sensitivities (S1(λ), S2(λ) and S3(λ)), which is a function equivalent to the XYZ color-matching function. This color information is more faithful to the sensitivity of the human eyes and has the higher accuracy, compared with color information obtained in RGB. The spectral sensitivities (S1(λ), S2(λ) and S3(λ)) have a small overlap, a sufficient S/N ratio and natural changes in spectral sensitivity curves. This minimizes the error in colorimetry.

The surface roughness of the image is recognizable separately from the color in the form of a histogram distribution. This enables the difference in roughness of the surface 5 to be accurately determined.

The following describes an example of test of three different samples having different roughnesses as shown in FIGS. 8A to 8C. The sample of the smallest roughness is a reference surface 1, the sample of the middle roughness is a test surface 2, and the sample of the largest roughness is a test surface 3. These surfaces 1 to 3 are subjected to the processing described above, and their distributions of xy chromaticity diagrams are created. Highlighted areas indicate integrated data in xy chromaticity diagrams of FIG. 8B. The integrated numbers H1 and H2 are expressed in lightness and darkness. The higher lightness indicates the larger integrated number. FIG. 8C is diagrams schematically showing the integrated numbers H1 and H2 of the reference surface and the test surfaces three-dimensionally. These diagrams show the chromaticities as the x and y axes and the integrated numbers H1 and H2 as the z axis. Basically, the larger irregularities provide a lower broader peak, and the smaller irregularities provides a sharper peak. The surface roughness index M that shows the degree of overlap is computed by comparing two histogram distributions of the reference surface 1 and the test surface 2 or 3. The irregularities in micron- or nano-order or in the higher order is determinable by the surface roughness index M.

The configuration of this embodiment performs colorimetry not one-dimensionally but two-dimensionally and allows for not only comparison of average values but statistical comparison. The configuration of this embodiment quantifies the roughness information complicated with the color information. The colorimetric values are obtained with regard to the respective pixels and are statistically processed in the form of a histogram.

The surface roughness index M is used for numerical comparison of the surface roughness such as emboss. Each colorimetric image is taken with the two-dimensional colorimeter. Because of the presence of frequency information, there are peaks in three-dimensional chromaticity diagrams as shown in the upper graphs of FIG. 9.

Figure 9:
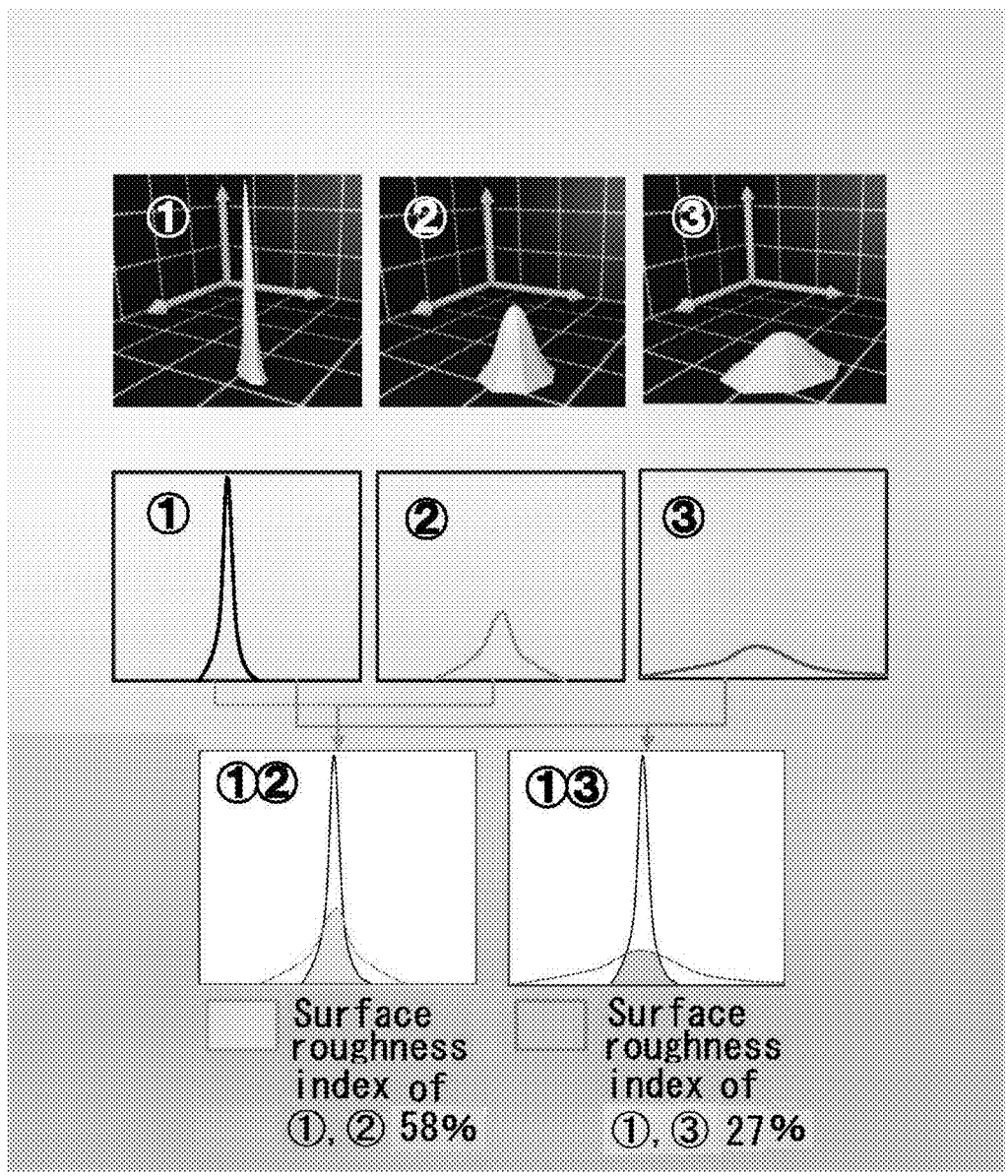
FIG. 9 is three-dimensional and two-dimensional diagrams showing surface roughness indexes.

In the upper diagrams of FIG. 9, (1) shows a concentrated sharp peak, (2) shows a standard peak, and (3) shows a broad gentle peak. The middle and lower graphs of FIG. 9 are obtained when these peaks are viewed horizontally. The graph (2) and the graph (3) are superimposed on the graph (1). The colored areas indicate overlaps. The volume ratio of this overlap is the surface roughness index M. The surface roughness index M is calculated, from the raw integrated numbers in the area of the examination area K, to be respectively 58% and 27% for the test surface 2 and the test surface 3 against the reference surface 1. This enables clear and easy determination of surface roughness by numerical values.

Figure 10:
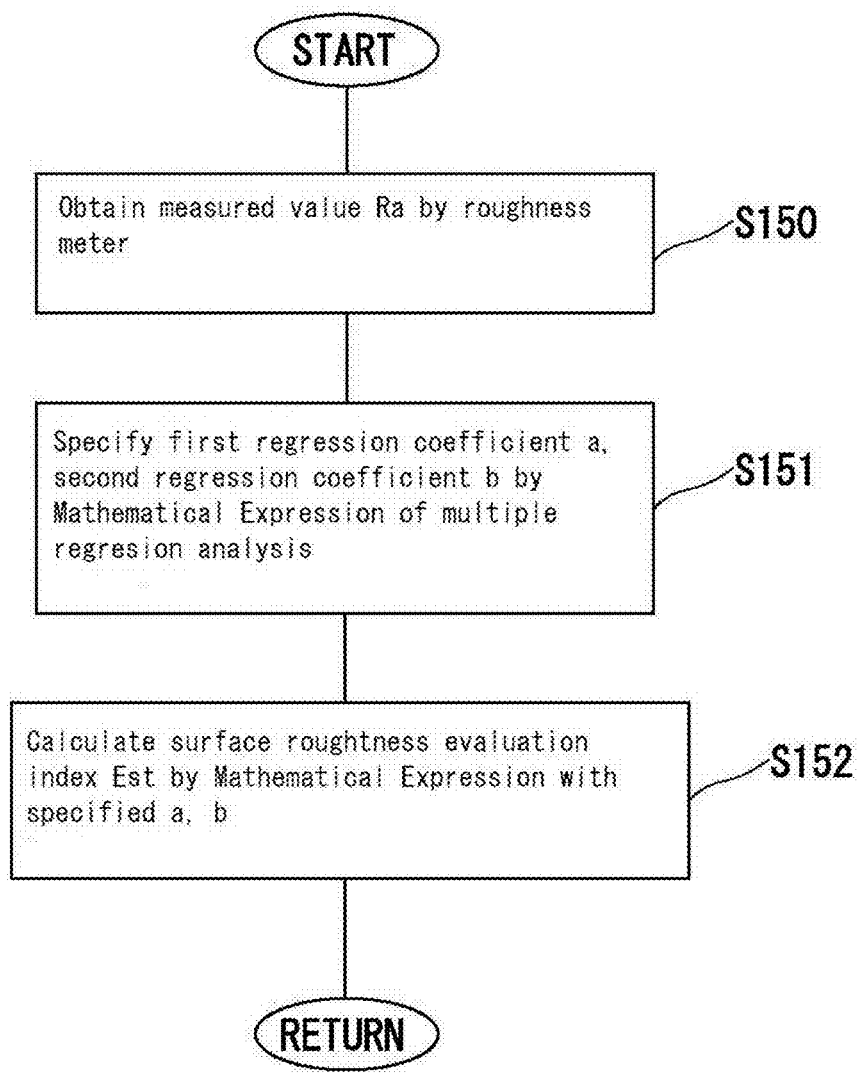
FIG. 10 is a flowchart (operation of multiple regression analysis) in an arithmetic processing unit 103 of a surface roughness determination apparatus 101 according to Embodiment 2 of the present disclosure.

When the surface roughness is in nano-order or in micron-order, a surface roughness evaluation index Est is calculated from the surface roughness index M and the color difference ΔE calculated as described above by multiple regression analysis as shown in FIG. 10. The surface roughness in nano-order or in-micron order is different from the large surface roughness by light scattering of the surface 5. The small roughness causes the interaction with light which the surface is irradiated with and thereby the interference of light and generates various shifts. The more accurate evaluation value is obtained by taking into account such shifts. Since the wavelength range of visible light is from 380 nm to 780 nm, color shift is observed more largely at the nano-level surface roughness close to the wavelength range. When the surface roughness is larger than the micron level compared with the wavelength of the light, diffraction of white light originating from the roughness is predominant over the shift of light, whether in the same material or different materials. In such a case, color shift may not be taken into account. The correlation of the surface roughness evaluation index to the measured value by the roughness meter is determined by multiple regression analysis by taking into account the shifts of the surface roughness index M and the color difference ΔE.

At the start of this processing, a measured value by a roughness meter is obtained with regard to an object of determination (S150). More specifically, a measured surface roughness value Ra is obtained by using a contact-type roughness meter.

A first coefficient a and a second coefficient b are specified to minimize the sum of errors Error by the least square method according to multiple regression analysis between Ra and Est expressed by Mathematical Expression 6 of given below (S151):

$$Est = a \cdot M + b \cdot \Delta E \qquad \text{(Math. 6)}$$

In Expression 6, Est denotes the surface roughness evaluation index, a denotes the first coefficient, M denotes the surface roughness index, b denotes the second coefficient, ΔE denotes the color difference.

The surface roughness evaluation index Est is calculated by substituting the calculated values M and ΔE into Mathematical Expression 6 with specified values of the coefficients a and b (S152).

Mathematical Expression 7 may be used in place of Mathematical Expression 6. This method is a simpler method without using the parameter of the color difference ΔE. The first coefficient a and the second coefficient b are specified to minimize the sum of errors Error by the least square method expressed by Mathematical Expression 8 according to multiple regression analysis between Ra and Est expressed by Mathematical Expression 7 of given below:

$$Est = a \cdot M + b \qquad \text{(Math. 7)}$$

In Mathematical Expression 7, Est denotes the surface roughness evaluation index, a denotes the first coefficient, M denotes the surface roughness index, b denotes the second coefficient.

$$\text{Error} = \Sigma (Est(i) - Ra(i))^2 \qquad \text{(Math. 8)}$$

In Mathematical Expression 8, Error denotes the error, Est denotes the surface roughness evaluation index, Ra(i) denotes the measured value by the roughness meter, i denotes the number of measured data.

The surface roughness evaluation index Est is calculated by substituting the calculated values M into Mathematical Expression 7 with specified values of the coefficients a and b (S152).

At least one of the first calibration curve function L1, the second calibration curve function L2 and the third calibration curve function L3 is set, based on the surface roughness index M, the color difference ΔE, the surface roughness evaluation index Est and the measured surface roughness value Ra measured or calculated as described above. All these functions L1 to L3 are set according to this embodiment. The function of the smallest error among the three functions or a combination of the functions of the smaller errors may be used. For determination of the roughness of the surface 5 as an object of determination, an image of the surface 5 as the object is taken, and the above respective functions are set based on the calculated surface roughness index M and the calculated color difference ΔE. The corresponding surface roughness evaluation index Est' and the measured surface roughness value Ra' (which are not actually measured values but are estimated values) are then determined according to the functions. This allows for the accurate evaluation of the surface roughness and thereby appropriate comparison and determination of the surface roughness relative to the reference surface, and accordingly prevents the occurrence of defective products. The details will be described later with reference to Examples 1 to 3.

Figure 11:
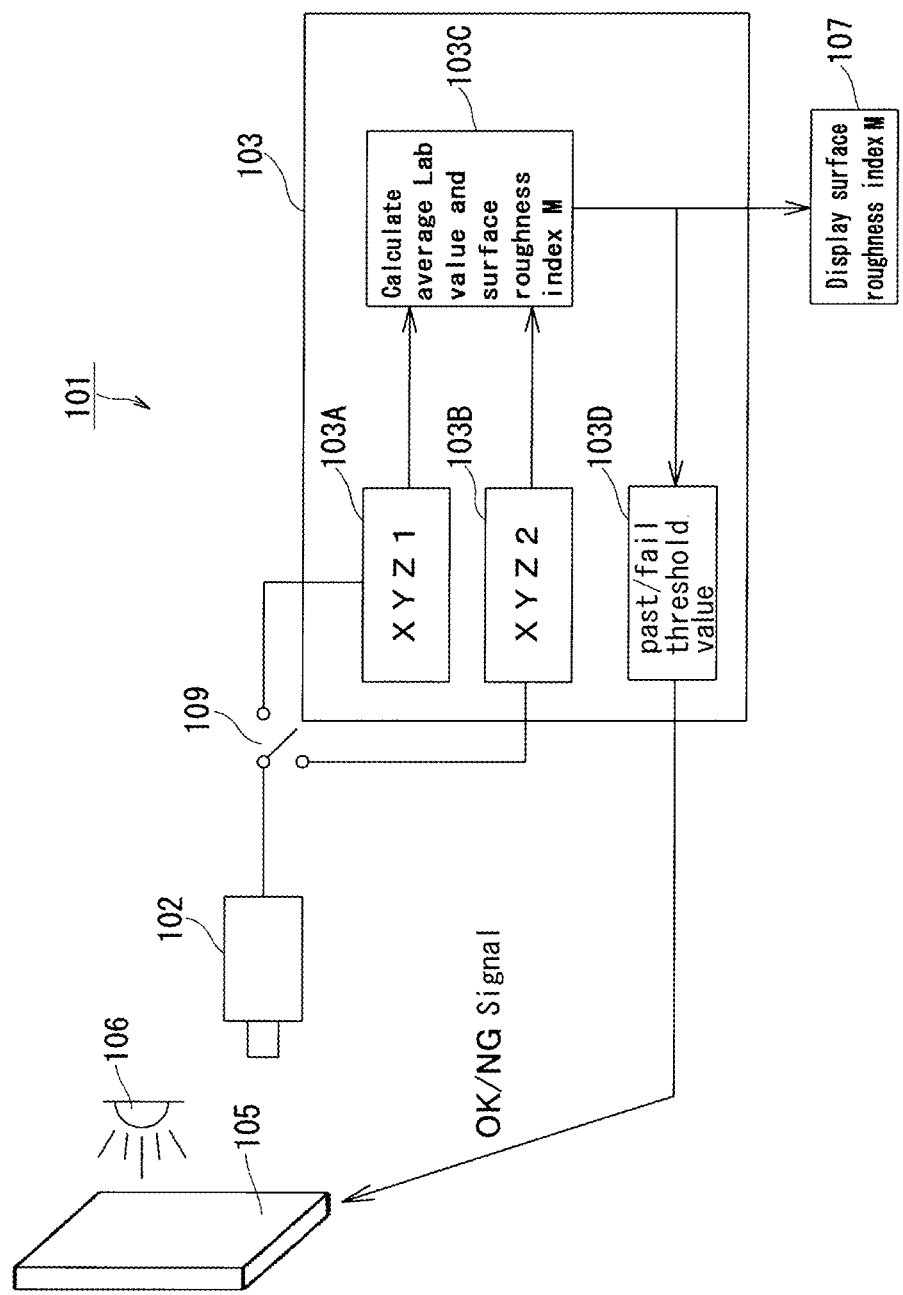
FIG. 11 is a block diagram illustrating the configuration of the surface roughness determination apparatus 101 according to Embodiment 2 of the present disclosure.
Figure 12:
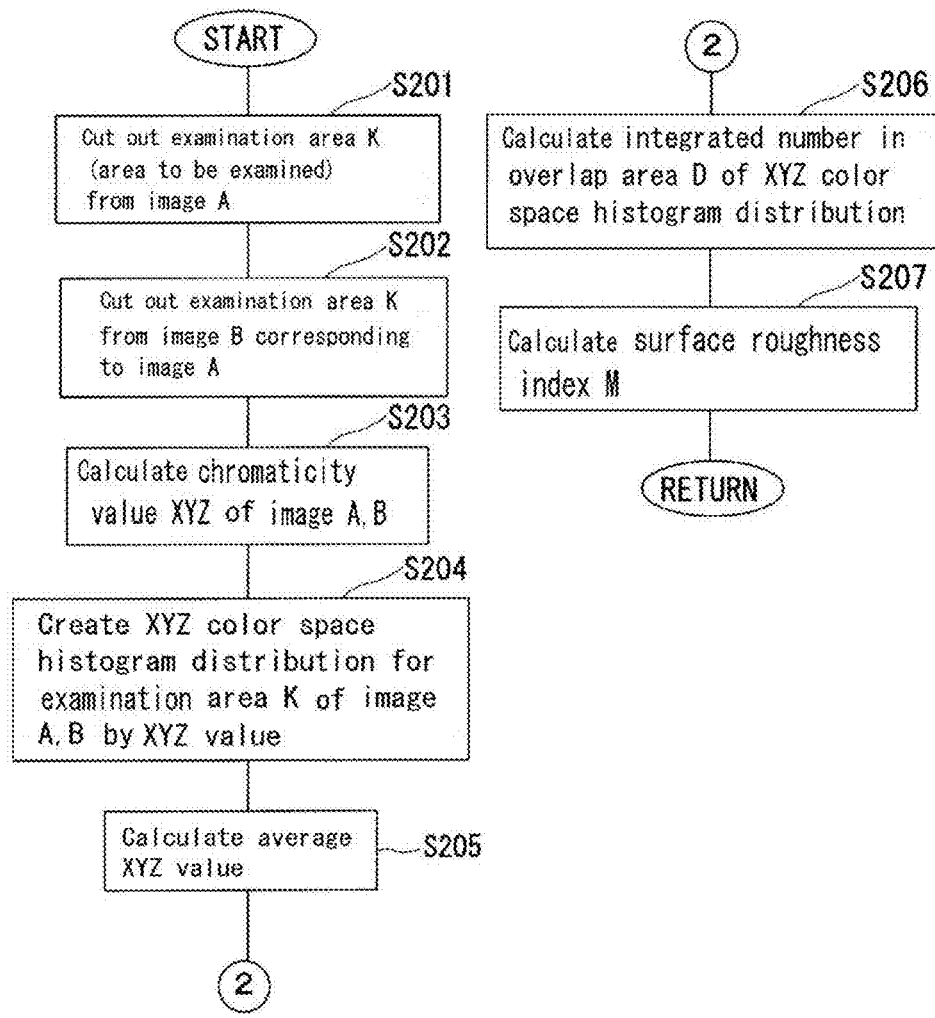
FIG. 12 is a flowchart (XYZ color space distribution) in the arithmetic processing unit 103 of the surface roughness determination apparatus 101 according to Embodiment 2 of the present disclosure.
Figure 13:
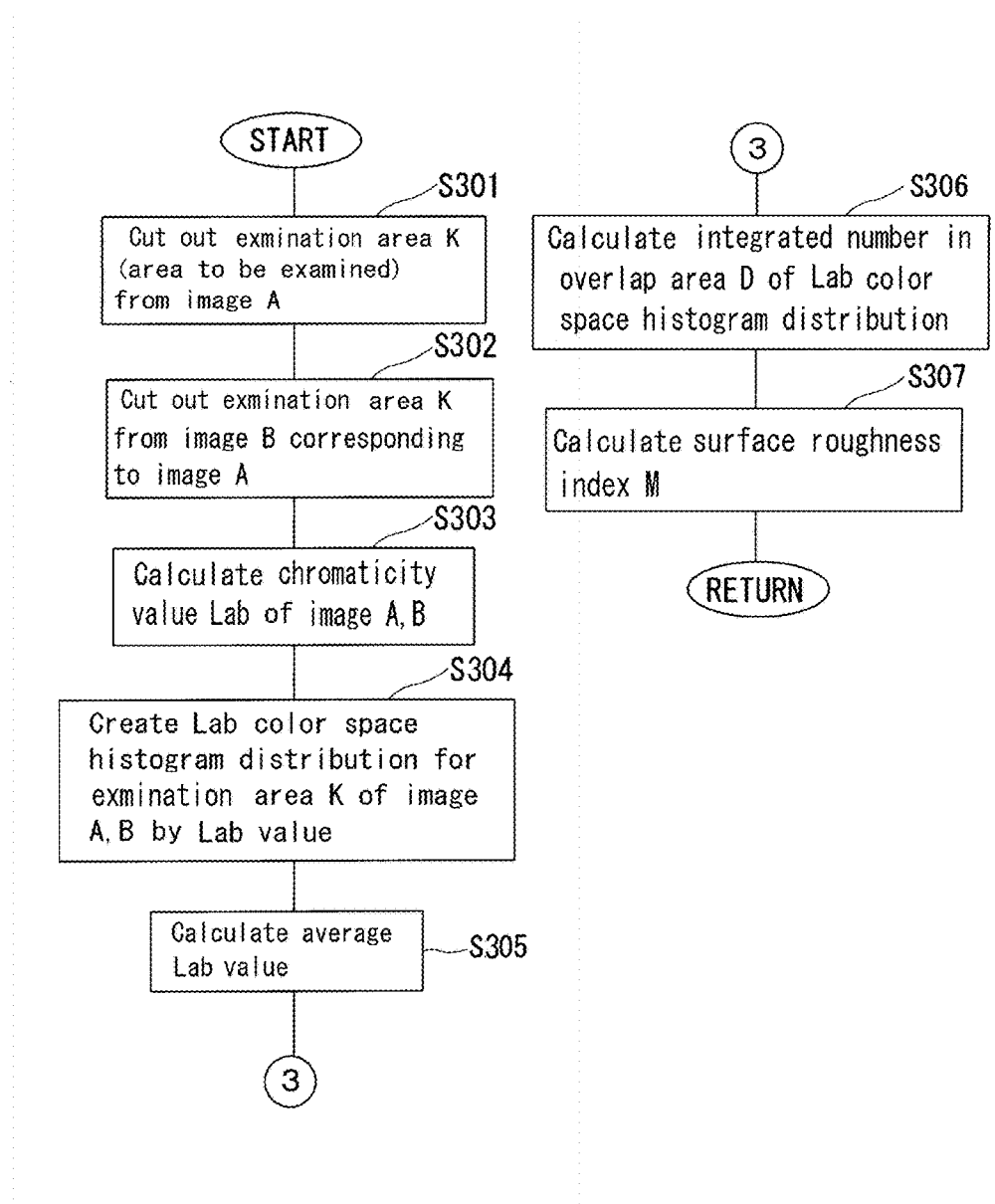
FIG. 13 is a flowchart (Lab color space distribution) in the arithmetic processing unit 103 of the surface roughness determination apparatus 101 according to Embodiment 2 of the present disclosure.

The following describes a surface roughness determination apparatus 101 for a surface 105 according to Embodiment 2 with reference to FIG. 11, FIG. 12 and FIG. 13. The corresponding like elements are expressed by the like numerals in 100s, and the differences are mainly described.

The surface roughness determination apparatus 101 includes a two-dimensional colorimeter 102 configured to take images of a reference surface and a test surface, an arithmetic processing unit 103 connected with the two-dimensional colorimeter 102 via a switch 109 and configured to receive signals and calculate a surface roughness index M, and a display device 107 connected with the arithmetic processing unit 103 and configured to display the index.

As shown in FIG. 11, the arithmetic processing unit 103 includes an operation part 103A configured to calculate a stimulus value XYZ1 obtained by imaging a reference surface, an operation part 103B configured to calculate a stimulus value XYZ2 obtained by imaging a surface 105 of a product as a test surface, and an operation part 103C connected with the operation part 103A and the operation part 103B and configured to calculate the surface roughness index M of the surface 105. An OK signal or an NG signal from the operation part 103C is sent to the display device 107 or to the outside. The switch 109 is operated for selective connection of the operation 103A or operation 103A with two-dimensional colorimeter 102.

FIG. 12 is a flowchart showing a process of calculating the surface roughness index M by comparison between chromaticity histogram distributions of two images A and B. As shown in FIG. 12, at the start of the program, the process cuts out, specifies and sets an examination area K of a test surface from the image A (S201). The process also cuts out, specifies and sets an examination area K of a reference surface from the image B (S202) in the same manner as that for the image A. The process calculates chromaticity value XYZ of the images A and B (S203). The process subsequently computes and creates XYZ color space histogram distributions of the test surface and the reference surface with regard to the respective examination areas K (S204), and calculates an average value of the chromaticity value XYZ (S205). The process specifies a minimum distribution of the XYZ color space histogram distributions and calculates an integrated number in an overlap area D of the XYZ color space histogram distributions (S206). The surface roughness index M is obtained as surface roughness index M=(integrated number of pixels included in the overlap area D/total number of pixels included in the examination area K)×100(%). The smaller integrated numbers between T1 and T2 are summed up as the integrated number in the overlap area D. The process then calculates the surface roughness index M (S207) and goes to Return.

In calculation of the XYZ distributions of the examination areas K, the surface roughness index M is calculated according to the distributions in the three-dimensional space of X axis, Y axis and Z axis. T1(X,Y,Z) and T2(X,Y,Z) respectively denote histograms of the test surface and the reference surface in the XYZ space coordinates. The histogram distribution is in a globe-like shape in the XYZ color space. The two histogram distributions may be sterically overlapped with each other or may be sterically separated from each other. The examination area K in the three-dimensional space is divided by grids G. Chromaticity histogram distributions of T1(X,Y,Z) and T2(X,Y,Z) and a minimum distribution are determined in the three-dimensional space, and the surface roughness index M is calculated. Another procedure may project the integrated numbers H1 and H2 of the grids G on a plane and similarly calculate the integrated number of the grids G in the overlap area D on the plane. The XYZ chromaticity histogram distribution does not include information on lightness. The histogram distribution does not change with a change in lightness of the image in the XYZ space.

The flowchart of FIG. 13 is used when Lab color space histograms are used for determination of the surface roughness, in place of the XYZ color space histograms. The above description of FIG. 12 is applied to the description of FIG. 13, and the corresponding like steps are expressed by like step numbers in 300s. The average Lab value in the examination area K of the image A and the average Lab value in the examination area K of the image B are calculated at S305. The Lab chromaticity histogram distribution includes information on lightness. The histogram distribution changes with a change in lightness of the image A or the image B in the Lab space.

Figure 14:
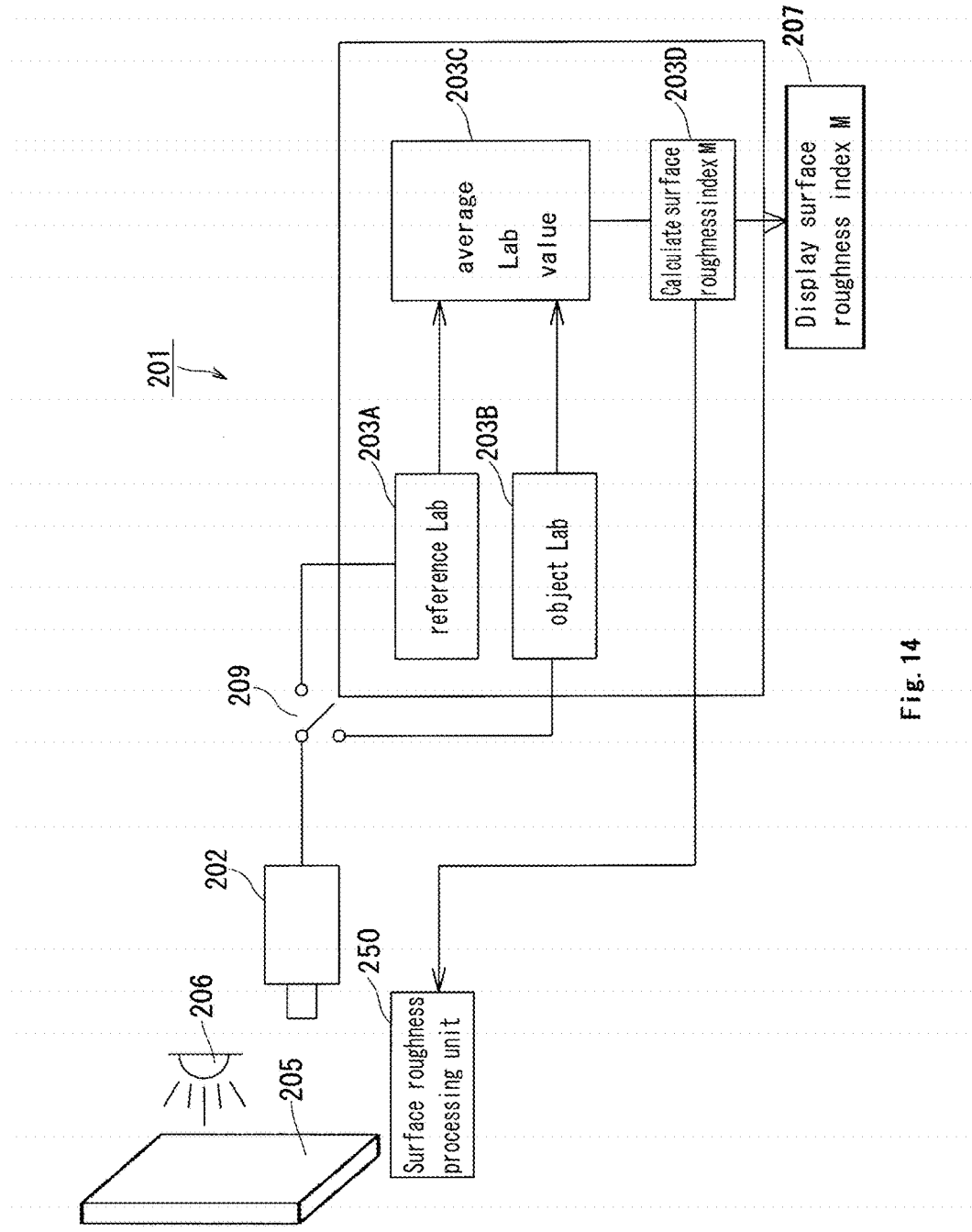
FIG. 14 is a block diagram illustrating the configuration of a surface roughness determination apparatus 201 according to Embodiment 3 of the present disclosure.

The following describes a surface roughness determination apparatus 201 for a surface 205 according to Embodiment 3 with reference to FIG. 14. The corresponding like elements are expressed by the like numerals in 200s, and the differences are mainly described.

As shown in FIG. 14, an object of color and roughness determination is a partial area of the surface 205. A two-dimensional colorimeter 202 is used to take an image of an examination area K of the surface 205. An arithmetic processing unit 203 includes an operation part 203A configured to calculate a Lab value from a stimulus value XYZ1 as a reference, an operation part 203B configured to calculate a Lab value from a stimulus value XYZ2 as an object of determination, an operation part 203C connected with the operation part 203A and the operation part 203B and configured to calculate an average Lab value, and a surface roughness index M operation part 203D configured to calculate a surface roughness index M from the reference Lab value and the object Lab value. The calculated values are sent from the operation parts 203C and 203D to a roughness processing unit 250. The roughness processing unit 250 checks the index value displayed on the screen to determine whether the surface roughness is appropriate and further performs roughness processing. A switch 209 is provided to selectively connect the operation part 203A or operation part 203B with the two-dimensional colorimeter 202. The primary processing flow is similar to those of the flowcharts of Embodiments 1 and 2 and is thus not specifically described.

In calculation of the chromaticity histogram distribution of the examination area K in the Lab space, the XYZ value is converted into a Lab value. The index is calculated according to the distributions in the three-dimensional space of the L axis, the a axis and the b axis. The Lab color space distribution is in an oval spherical shape. U1(L,a,b) and U2(L,a,b) respectively denote histograms of the test surface and the reference surface in the Lab space coordinates. The histogram distribution is in a globe-like shape in the Lab color space. The two histogram distributions may be sterically overlapped with each other or may be sterically separated from each other. The examination area K in the three-dimensional space is divided by grids G. Color space histogram distributions of U1(L,a,b) and U2(L,a,b) and a minimum distribution are determined in the three-dimensional space, and the surface roughness index M is calculated. Another procedure may project the integrated numbers H1 and H2 of the grids G on a plane and similarly calculate the integrated number of the grids G in the overlap area D on the plane. The Lab color space histogram distribution includes information on lightness. The L value changes with a change in the lightness of the image A or the image B in the Lab space. The histograms U1 and U2 accordingly shift in position in the Lab space. This ensures determination by taking into account the lightness. This is because the difference in lightness of the image A or the image B shifts the position of the distribution. For example, the Lab color space histogram distribution is shifted downward with an increase in darkness and is shifted upward with an increase in lightness.

There are other applications. The two obtained images A and B of the reference surface and the test surface may be superimposed, and their respective chromaticity histogram distributions may be displayed on the display device 7. The respective chromaticity histogram distributions may be superimposed on one chromaticity diagram, and the difference in color may be specified by the average Lab value. The surface roughness index M showing the roughness of the surface 5 may be separately determined and displayed in percentage. This configuration enables the irregularities and the roughness of the surface to be numerically expressed by a difference of the chromaticity distribution of the test surface relative to the chromaticity distribution of the reference surface in the space. The results of examination may be numerically displayed with regard to the respective areas K. The width of the grid G may be adjustable. The reference value of the index may be set arbitrarily. The results of measurement and the images A and B may be stored. The configuration reduces the potential problem of individual variation and the potential trouble caused by a difference from the criterion employed by the client, which are inevitable in visual examination and achieves standardization for the finishing degree of surface roughness and stable surface roughness management.

The following describes a surface roughness determination apparatus and surface roughness determination method using a white light source according to Embodiment 4 with reference to FIG. 15 to FIG. 19. Embodiment 4 is basically similar to Embodiments 1 to 3. The explanation about the similar configurations in Embodiments 1 to 3 is applicable to Embodiment 4.

Offset is not used for calculating the surface roughness index M in Embodiments 1 to 3. In the cases where the material of the object for calibration data and the material of the two-dimensional object to be measured are same, more accurate roughness data can be obtained because the calibration data are made from both the parameters of color change and color distribution change. On the other hand, an offset value is used in Embodiment 4. Embodiment 4 is a method of obtaining a calibration curve only from the matching degree of the color distribution corrected by an offset value, when it is not sure if the metallic material of the object to be measured are the same as the material of the object for the calibration.

In Embodiments 1 to 3, intrinsic color of the materials are not changed while irregularities are made on metallic materials or composite materials by etching or the like, and accordingly calibration plates made of the same materials are used. In Embodiment 4, calibration plates made of different materials are used to make a calibration curve. For example, sold calibration plates as standard of surface roughness can be used as the calibration plates. When using commercially available calibration plates, and when their roughness values are known, their roughness values can be used as Ra values.

Surface roughness measurement procedure in Embodiment 4 is as follows. (a) Ra values of the calibration plates are measured by a mechanical type roughness meter. (b) Surface roughness index M is calculated. Where, the calculation is performed without offset correction when the material of the object to be measured is the same as the material of the object for calibration, and the calculation is performed with offset correction when the material of the object to be measured is not known.

When the metallic material of the object to be measured is the same as the material of the object for calibration, color variations ($\Delta E$, $\Delta b$ or the like) are also used as a parameter for calibration line (curve). On the other hand, when the intrinsic color of the material is not known, a fourth calibration curve is made only from the surface roughness index M (matching degree) with color offset. This is the added function as Embodiment 4.

Figure 38:
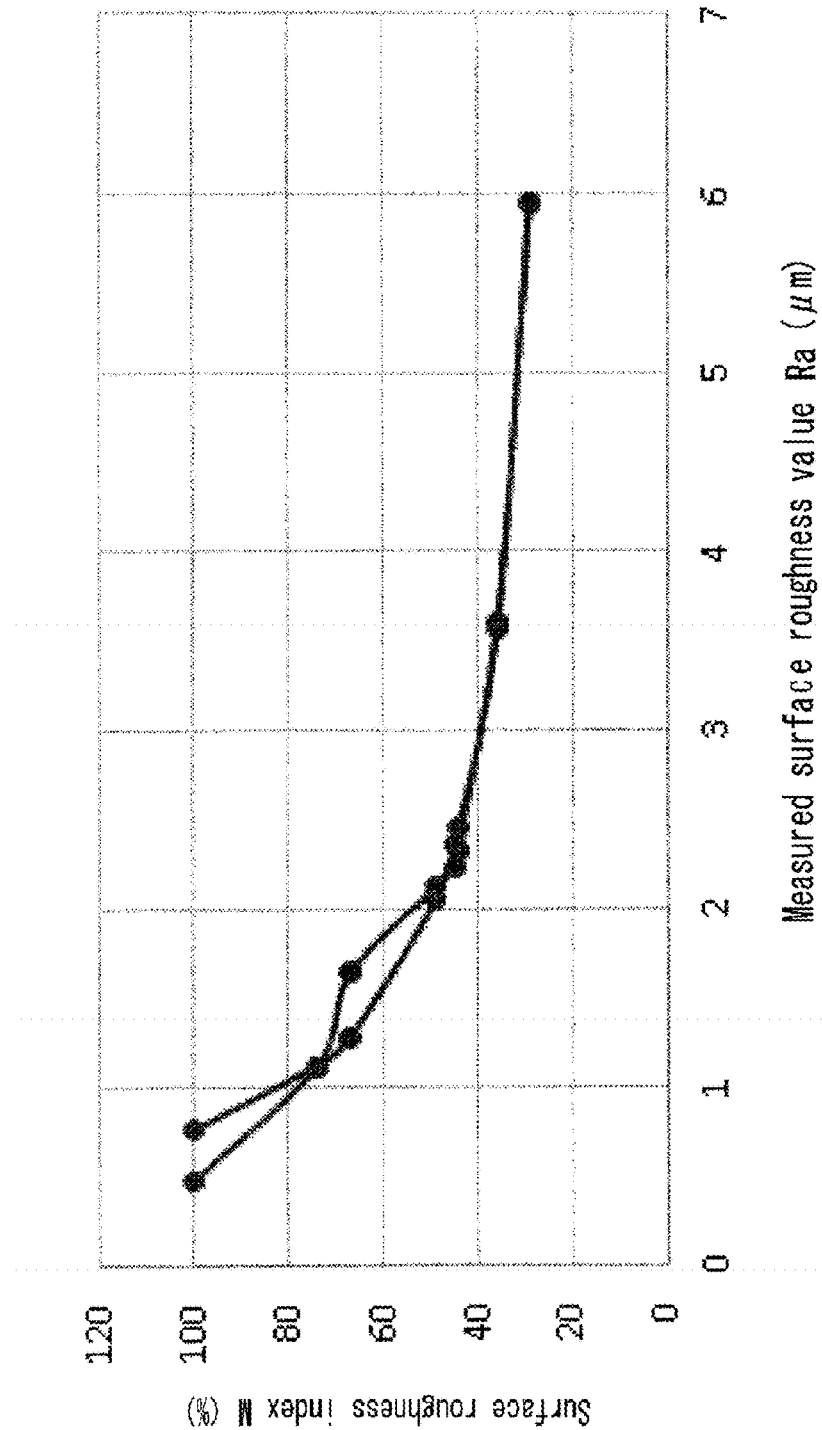
FIG. 38 is a graph showing a data to make a fourth calibration curve of Example 4.

For the data shown in FIG. 38, a calibration curve of Ra=A/(M−B) was set and calculated by using an optional function, Solver, of Excel (a convenient function of calculation using least-square method with regard to a set function) to determine A and B. A was determined to be 62.31 and B was determined to be 18.526. And a calibration curve of Ra=62.31/(M−18.526) was thus obtained. Ra is actually mechanically measured value Ra, which is the surface roughness value prescribed by JIS. Ra is measured by a mechanical type roughness meter. Definition is described in JIS. A and B are calibration coefficients.

Figure 15:
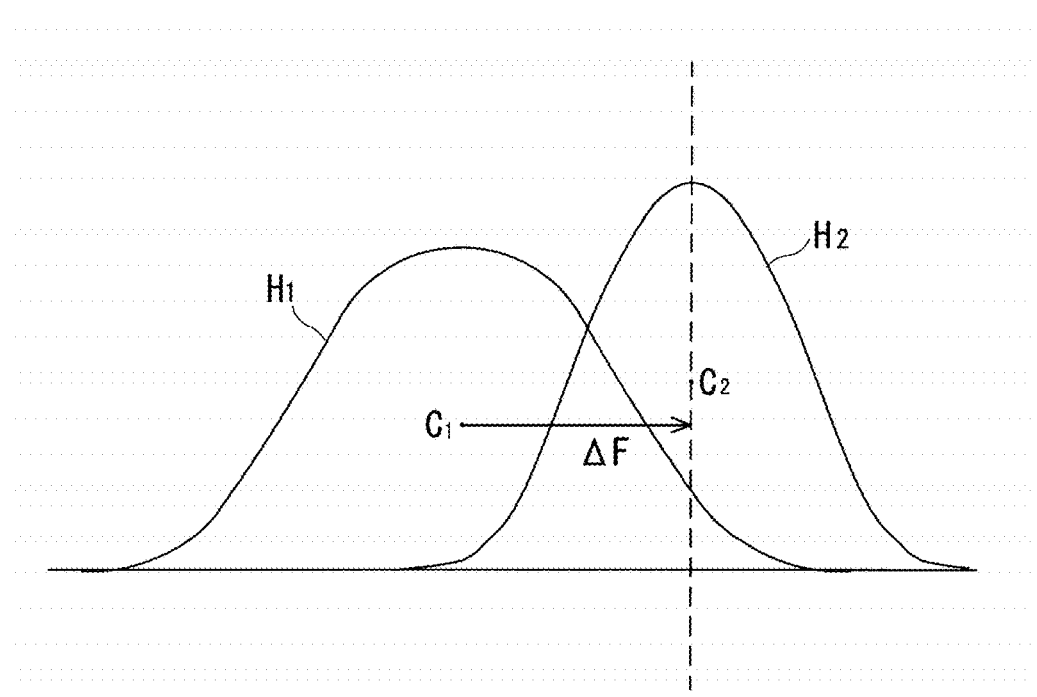
FIG. 15 is a diagram illustrating an offset process in an xy chromaticity diagram by the arithmetic processing unit according to Embodiment 4 of the present disclosure.
Figure 16:
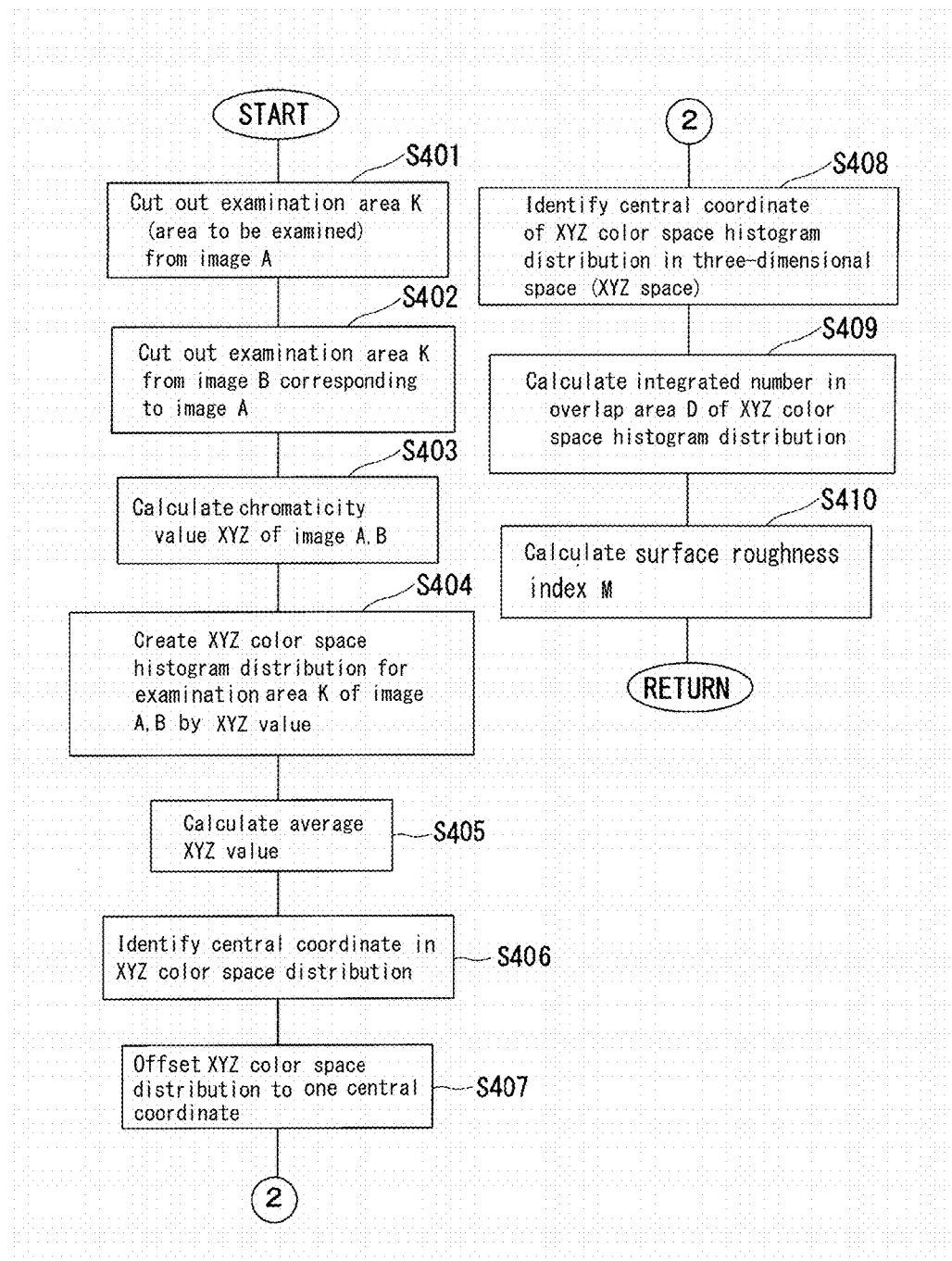
FIG. 16 is a flowchart (XYZ color space distribution) in the arithmetic processing unit according to Embodiment 4 of the present disclosure.
Figure 17:
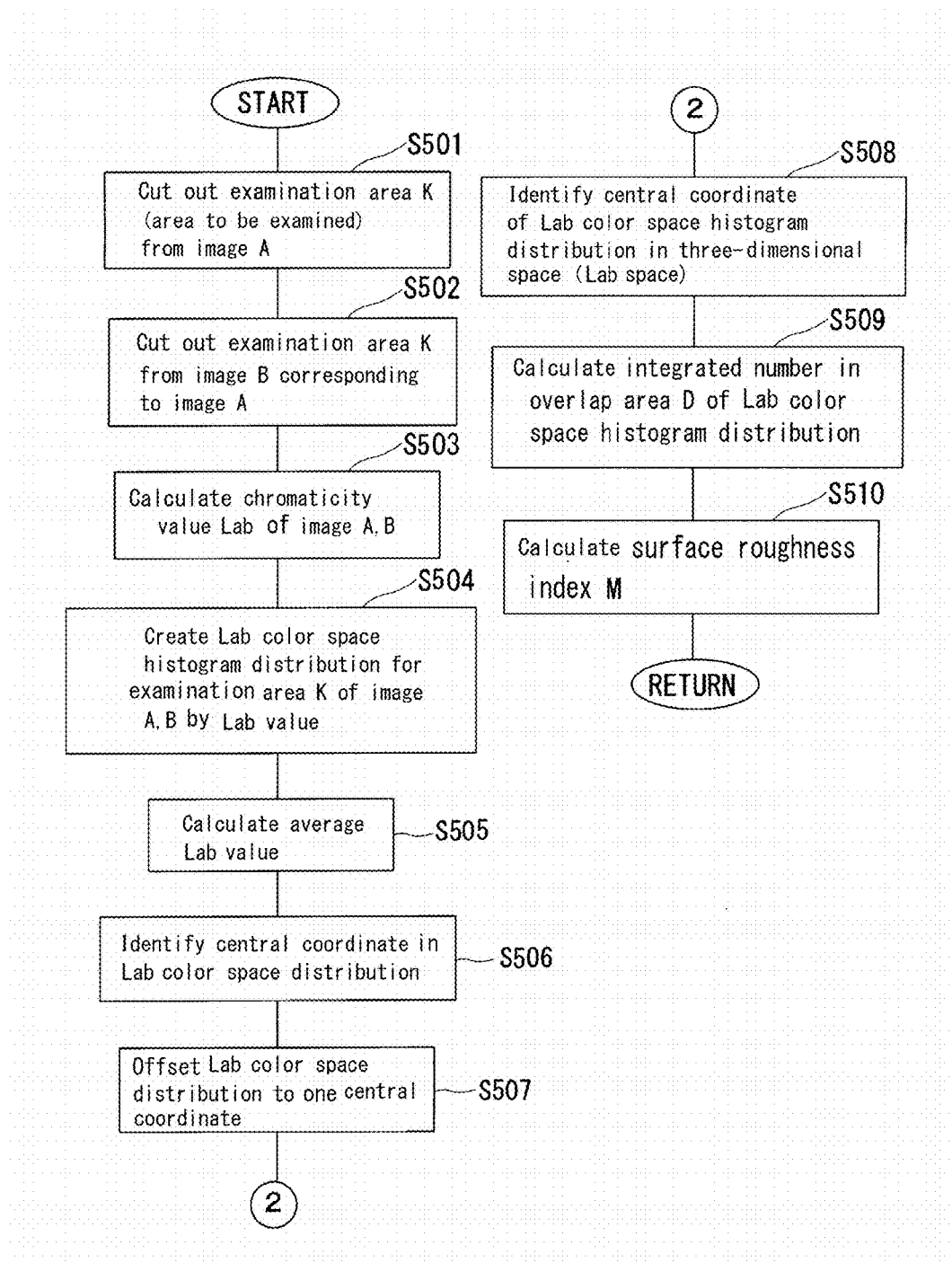
FIG. 17 is a flowchart (Lab color space distribution) in the arithmetic processing unit according to Embodiment 4 of the present disclosure.
Figure 18:
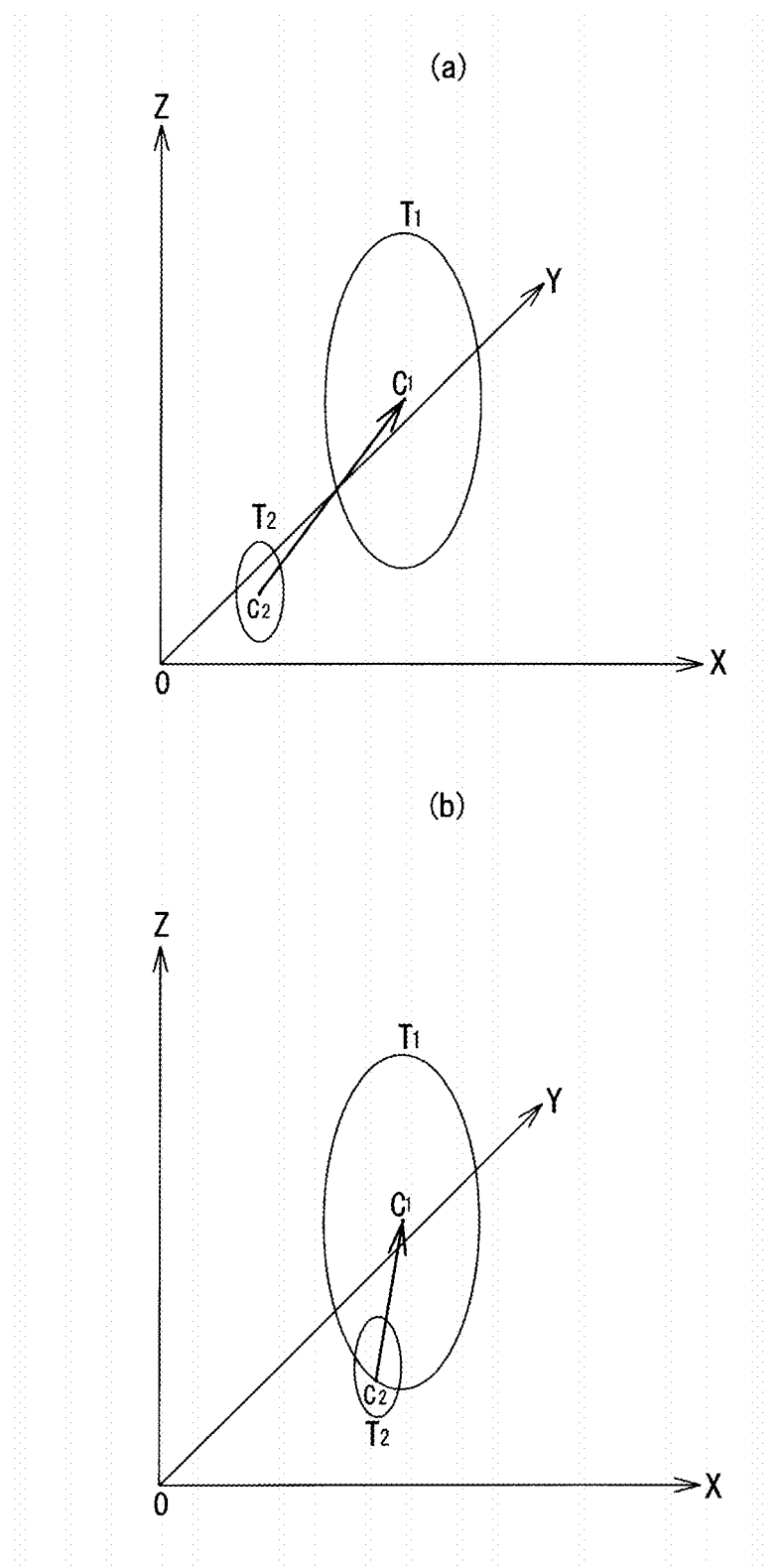
FIG. 18 is a diagram illustrating an offset process in an XYZ color space according to Embodiment 4 of the present disclosure.

The following describes an offset correction with reference to FIG. 15 to FIG. 19. The process offsets (maps) the entire XYZ color space histogram distribution by a deviation $\Delta F$ of the central coordinates, such that one of central coordinates of two XYZ color space histogram distributions T1(X,Y,Z) and T2(X,Y,Z) matches with the other central coordinate (S407) as shown in FIG. 16 and FIG. 18. A difference in color component is calculated without such an offset of one distribution to the other distribution. The distribution may be offset on the graph or may be offset by calculation. The amount of the offset may be set appropriately. An offset of one center into a predetermined range around the other center has similar effects as those of an offset of one center to the other center. There is accordingly a need to bring the two distributions closer to each other by an appropriate amount of offset that enables the roughness to be evaluated.

The process identifies central coordinates C1 and C2 in the XYZ color space histogram distributions (S406, S408) before and after the offset process (S407). The central coordinate herein denotes a centroid (center of gravity). Difference between FIG. 12 and FIG. 16 is inserted three steps of S406 to S408.

Figure 19:
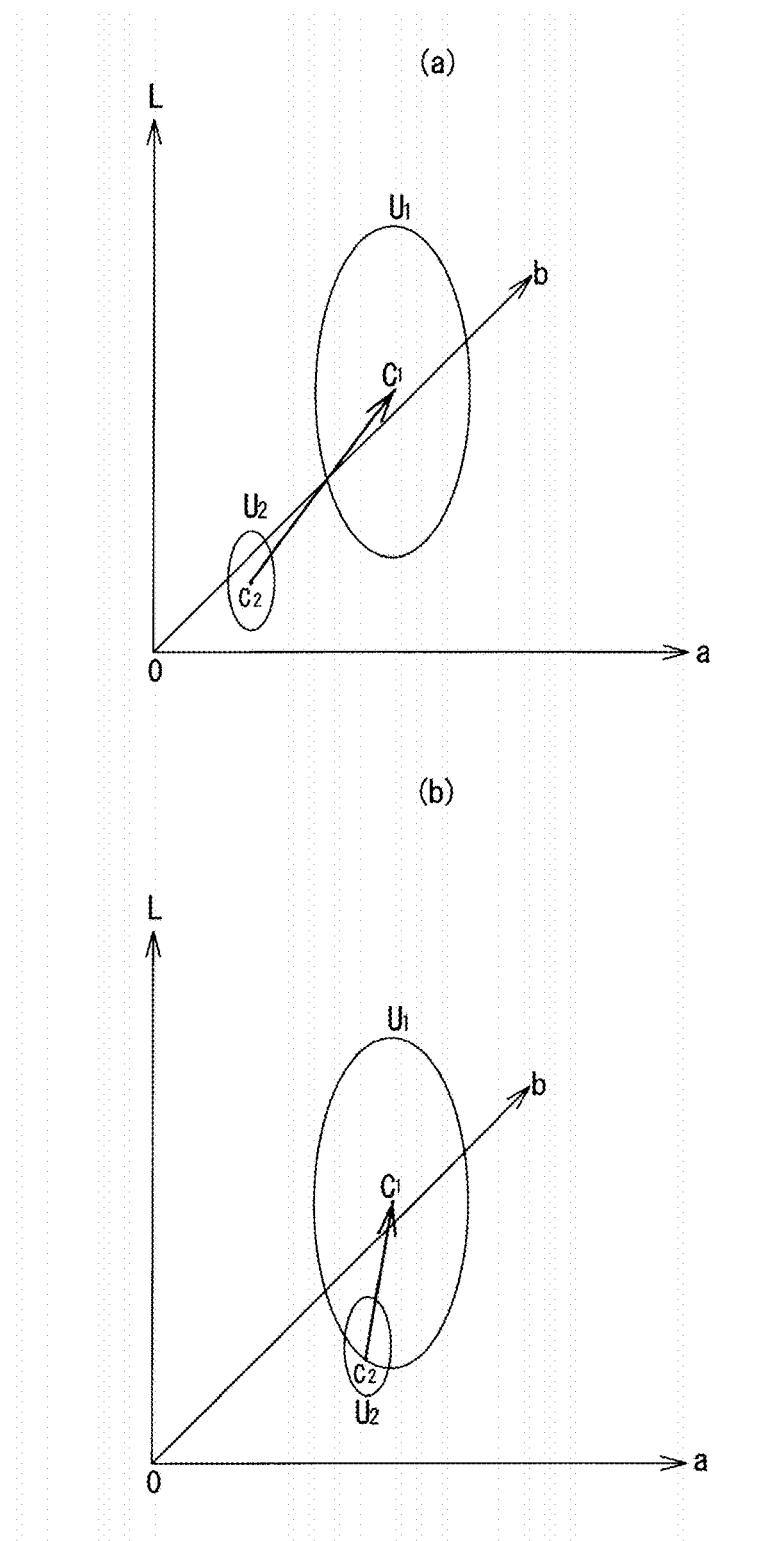
FIG. 19 is a diagram illustrating an offset process in an Lab color space according to Embodiment 4 of the present disclosure.

The flowchart shown in FIG. 17 is used when using Lab color space histograms shown in FIG. 19 for surface roughness determination instead of the XYZ color space histograms. The above explanation of FIG. 16 is also applicable to FIG. 17. When using xy chromaticity histograms, offset is performed as shown in FIG. 15. Flowchart for xy chromaticity histograms is omitted.

The embodiments 1 to 4 described above have the following advantageous effects. The embodiments describe the calculation of the color difference $\Delta E$ and the surface roughness index M with regard to (1) average L value, average a value and average b value or (2) two values H1(x,y) and H2(x,y), T1(X,Y,Z) and T2(X,Y,Z) or U1(L,a,b)

and U2(L,a,b). The configurations of these embodiments enable the difference in surface roughness to be provided separately from the color. This allows for accurate and prompt evaluation and provides the appropriate guideline for surface finishing by adjustment of the surface roughness.

The embodiments allow for determination of small surface roughness having the height of irregularities in the nanometer-order level to the micrometer-order level and enables the roughness of s curved surface and the roughness of a product having a large area to be accurately determined, while shortening the measurement time.

Additionally, accurate measurement of surface roughness becomes possible when the material of an object to be measured are not known, because calculation is performed with the offset correction in such a case.

The surface roughness determination apparatus 1 of the present disclosure was used for measurement and evaluation of the roughness of the surface 5 as described in Example 1 to Example 3. The present disclosure is described more specifically with reference to these examples but is not limited to these examples in any sense. The characteristic values were measured and evaluated in these examples as described below.

Example 1

(1) Determination Apparatus

A determination apparatus PPLB-200 manufactured by PapaLab Co., Ltd. was used. The determination apparatus PPLB-200 includes a two-dimensional colorimeter RC-500. A lighting device D50 manufactured by Panasonic Corporation was used for illumination.

(2) Imaging

Imaging was performed with PPLB-200 in a dark room. The two-dimensional colorimeter used was a still image type. The measurement was performed with the L value of a white board set to 100.

(3) Measurement Range

The measurement range of each sample was the entire image A and the entire image B in Examples 1, 2, and 3.

(4) Roughness Meters

The roughness meters used in Examples 1, 2 and 4 were a roughness meter FORM TALYSURF (registered trademark) 120 (AFM contact type) manufactured by Taylor Hobson Ltd. and the roughness meter used in Example 3 was a contactless roughness meter VN-8010 manufactured by KEYENCE CORPORATION.

(5) Measurement Items and Results

Measurement was performed for a reference surface of a sample and a test sample. Images A and B of the test sample and the reference sample were taken, and the surface roughness index M, ΔE, and the difference of the average Lab value of the images A and B were determined. The surface roughness index M is a value obtained without offset of center coordinates in a histogram distribution. The difference of average Lab value is equal to (average Lab value of the test sample)−(average Lab value of the reference sample). A sample having the highest similarity to the reference sample with regard to both the color and the surface roughness of the surface 5 was specified according to the results of the surface roughness index and ΔE of the measurement results. A value ΔE00 that takes into account the human visibility characteristic was used as ΔE.

The surface roughness index M, Lab, ΔL, Δa, Δb, and ΔE were determined with regard to samples 1 and 2 of Example 1 and sample 3 of Example 2 and sample 4 of Example 3. The surface roughness index M is an index calculated without offsetting of center coordinates in respective histogram distributions. Lab denotes a surface roughness index in the Lab coordinates, M denotes a surface roughness index in the xy coordinates. ΔL denotes a difference in average L value=(average L value of test sample)−(average L value of reference sample). ΔE, Δa and Δb are similarly calculated. A sample 2 or a sample 3 having the highest similarity to the sample 1 with regard to both the color and the surface roughness was specified according to the results of the surface roughness index and ΔE of the measurement results. A value ΔE00 that takes into account the human visibility characteristic was used as ΔE.

(6) Setting of Calibration Curves

Calibration curves between Ra and Est, Ra and ΔE, Ra and M in Example 1 and calibration curves between Ra and M, Ra and Est in Example 3 are calculated according to multiple regression analysis. Example 1 performed multiple regression analysis for evaluation of the roughness in micron-order. Example 3 performed multiple regression analysis for evaluation of the roughness in nano-order.

With regard to the calibration curves between Ra and Est the coefficients a and b were set to minimize the error by the least square method according to multiple regression analysis, using Mathematical Expressions 6 and 7 for Est.

Example 1 made evaluation for the roughness of samples of aluminum alloy treated by chemical etching.

Figure 20:
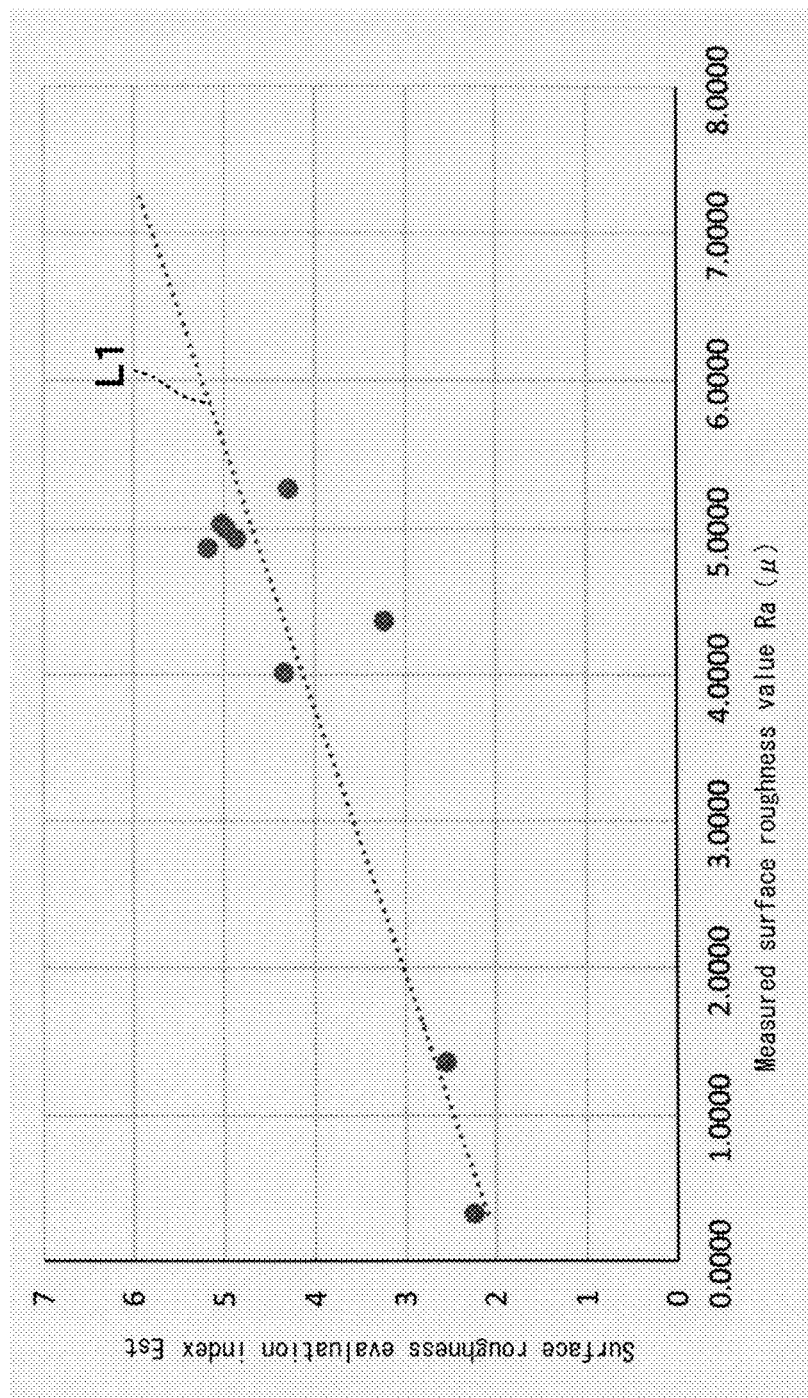
FIG. 20 is a graph 1 showing a variation in surface roughness evaluation index Est against measured surface roughness value Ra with regard to a metal sample 1 of Example 1.
Figure 21:
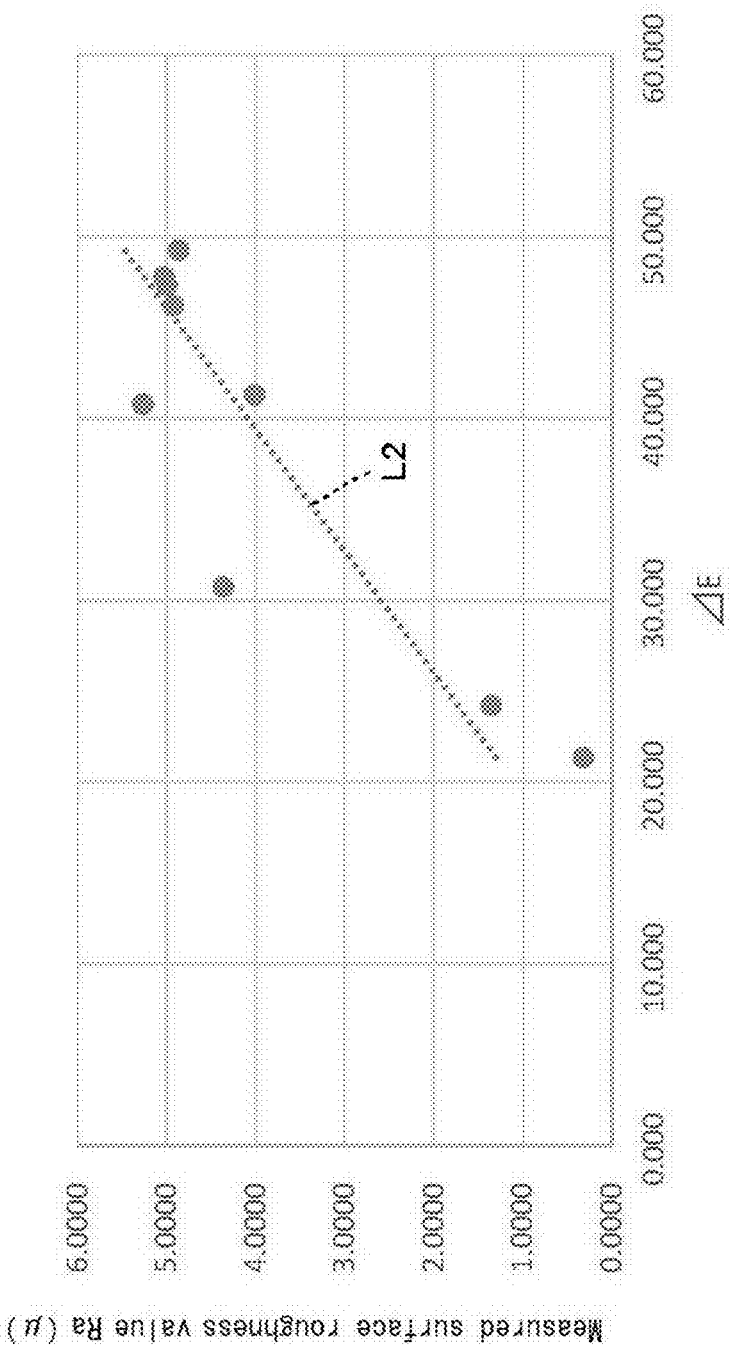
FIG. 21 is a graph 2 showing a variation in measured surface roughness value Ra against color difference ΔE with regard to the metal sample 1 of Example 1.
Figure 22:
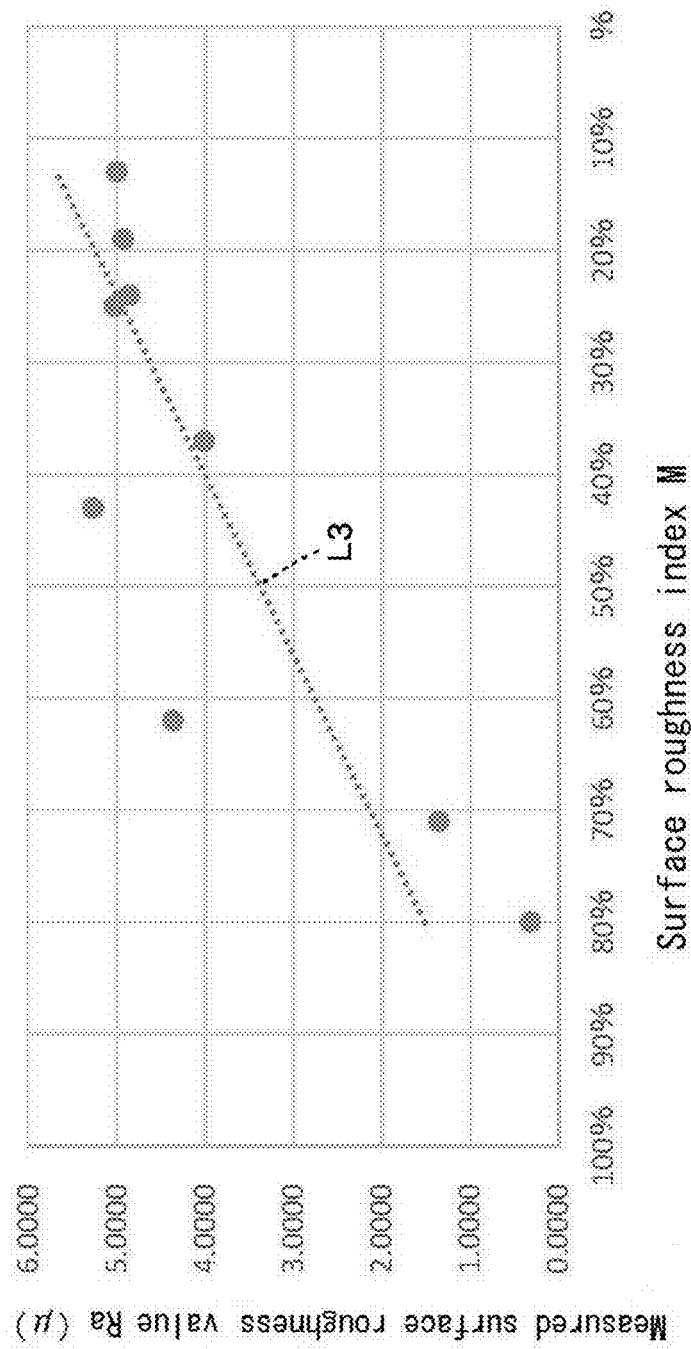
FIG. 22 is a graph 3 showing a variation in measured surface roughness value Ra against surface roughness index M with regard to the metal sample 1 of Example 1.

Table 1 and FIG. 20 to FIG. 22 show the results of measurement and calculation of the sample 1. FIG. 20 shows the measured surface roughness value Ra (unit of μm) as the abscissa and the surface roughness estimation index Est as the ordinate, and a dotted straight line is the first calibration curve L1. FIG. 21 shows the color difference ΔE as the abscissa and the measured surface roughness value Ra (unit of μm) as the ordinate, and a dotted straight line is the second calibration curve L2. FIG. 22 shows the surface roughness index M as the abscissa and the measured surface roughness value Ra (unit of μm) as the ordinate, and a dotted straight line is the third calibration curve L3.

TABLE 1

| Sample No. 1 | Index M | ΔE | Ra | Est | Error |
|---|---|---|---|---|---|
| NO. 11 | 80% | 21.358 | 0.3236 | 2.247753 | 1.9242 |
| NO. 12 | 71% | 24.221 | 1.3598 | 2.54906 | 1.1893 |
| NO. 13 | 62% | 30.754 | 4.3674 | 3.236604 | 1.1308 |
| NO. 14 | 43% | 40.810 | 5.2691 | 4.294915 | 0.9742 |
| NO. 15 | 37% | 41.298 | 4.0143 | 4.346273 | 0.3320 |
| NO. 16 | 24% | 49.261 | 4.8679 | 5.184312 | 0.3164 |
| NO. 17 | 25% | 47.807 | 5.0313 | 5.031291 | 0.0000 |
| NO. 18 | 19% | 46.234 | 4.9311 | 4.865746 | 0.0654 |
| NO. 19 | 13% | 47.337 | 5.0013 | 4.981827 | 0.0195 |
| | | | | TotErro | 5.9516 |

The results obtained were a=0 and b=0.105242. The correlation coefficient of the surface roughness evaluation index Est and the measured surface roughness value Ra was 0.887104. The correlation coefficient of the color difference ΔE and the measured surface roughness value Ra was 0.887104. The correlation coefficient of the surface roughness index M and the measured surface roughness value Ra was −0.8377. The total error TotErro was 5.9516.

The sample 2 of Example 1 was samples of aluminum alloy treated by chemical etching.

Figure 23:
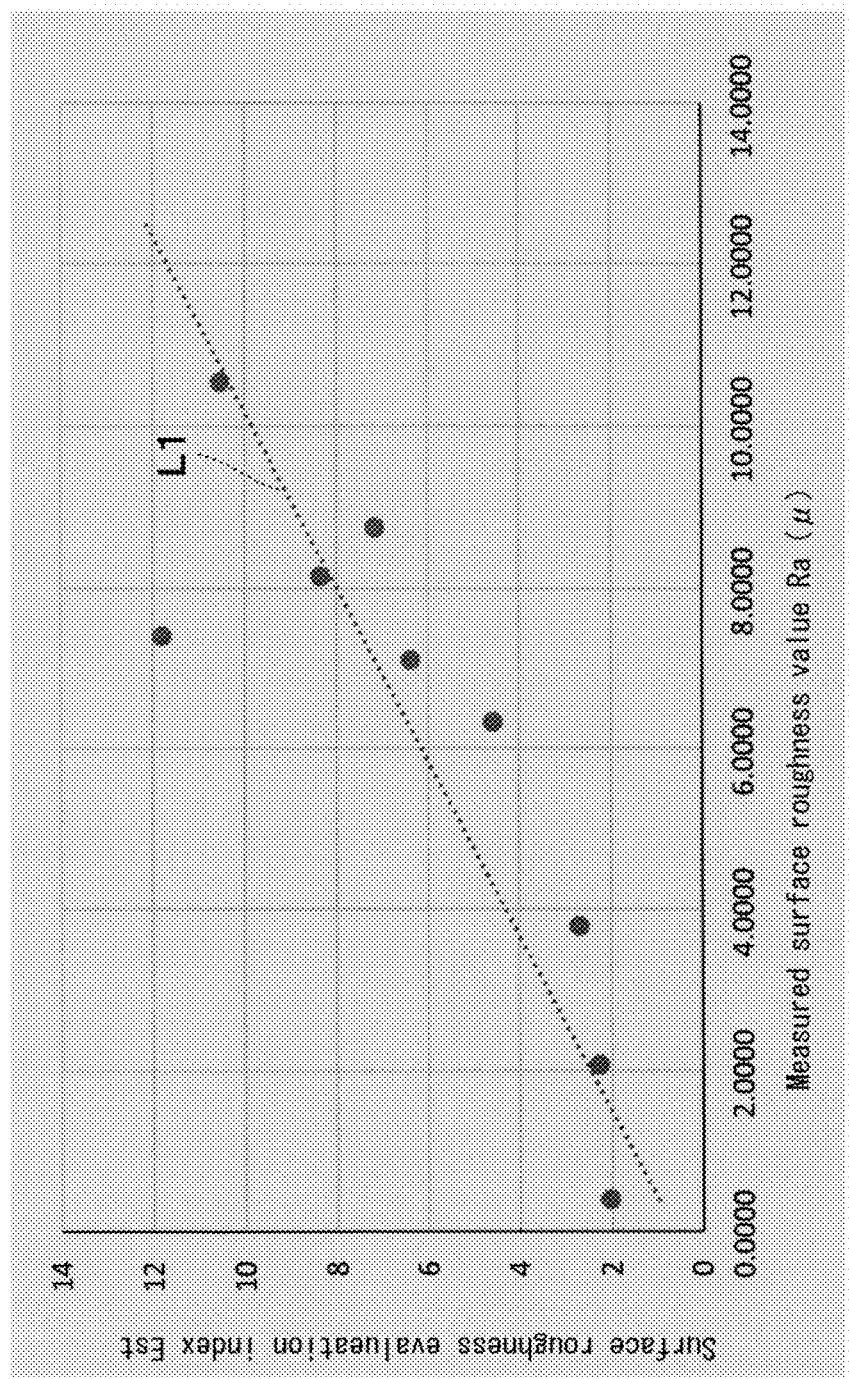
FIG. 23 is a graph 1 showing a variation in surface roughness evaluation index Est against measured value Ra by a with regard to a metal sample 2 of Example 1.
Figure 24:
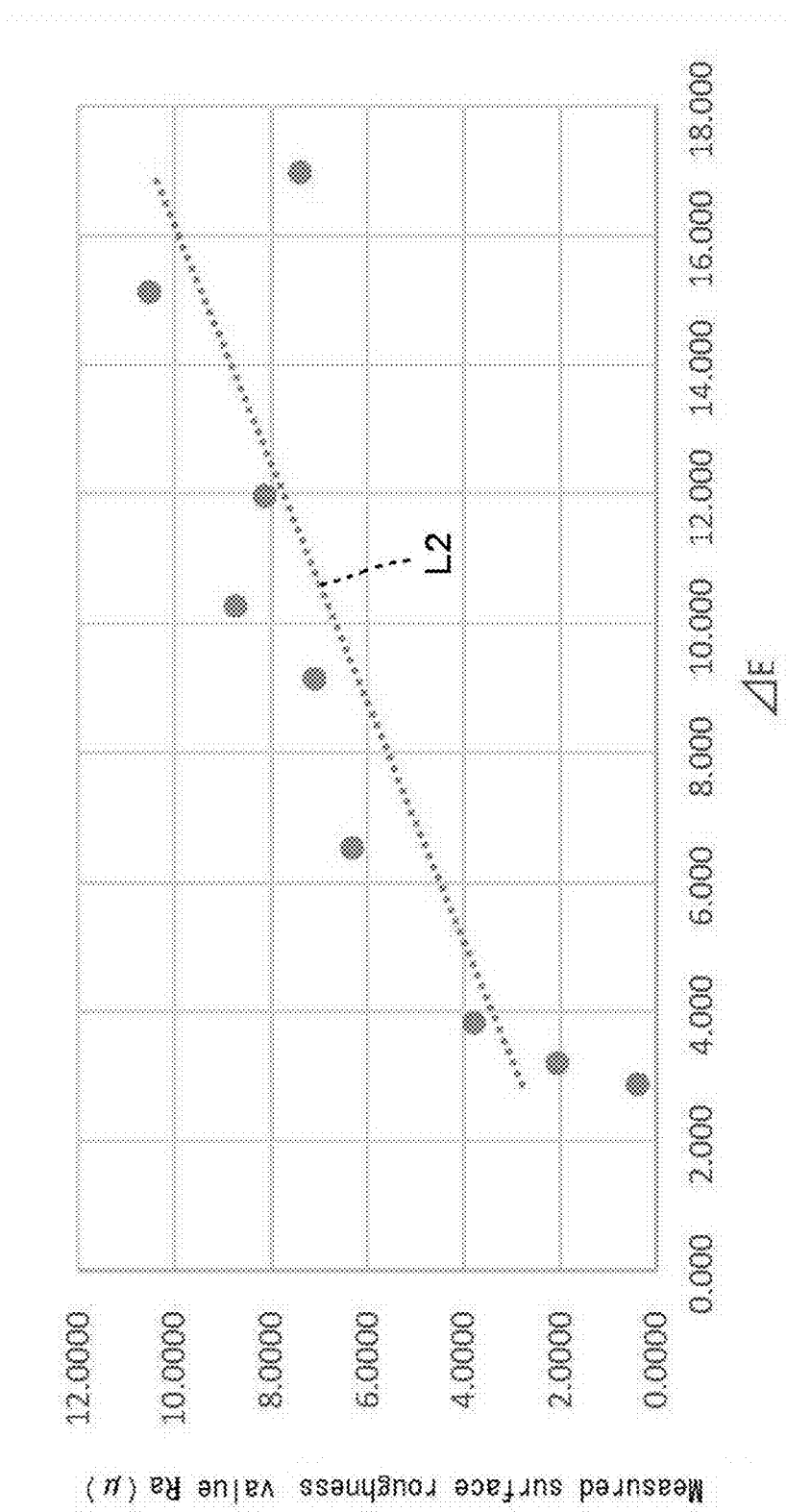
FIG. 24 is a graph 3 showing a variation in measured surface roughness value Ra against color difference ΔE with regard to the metal sample 2 of Example 1.
Figure 25:
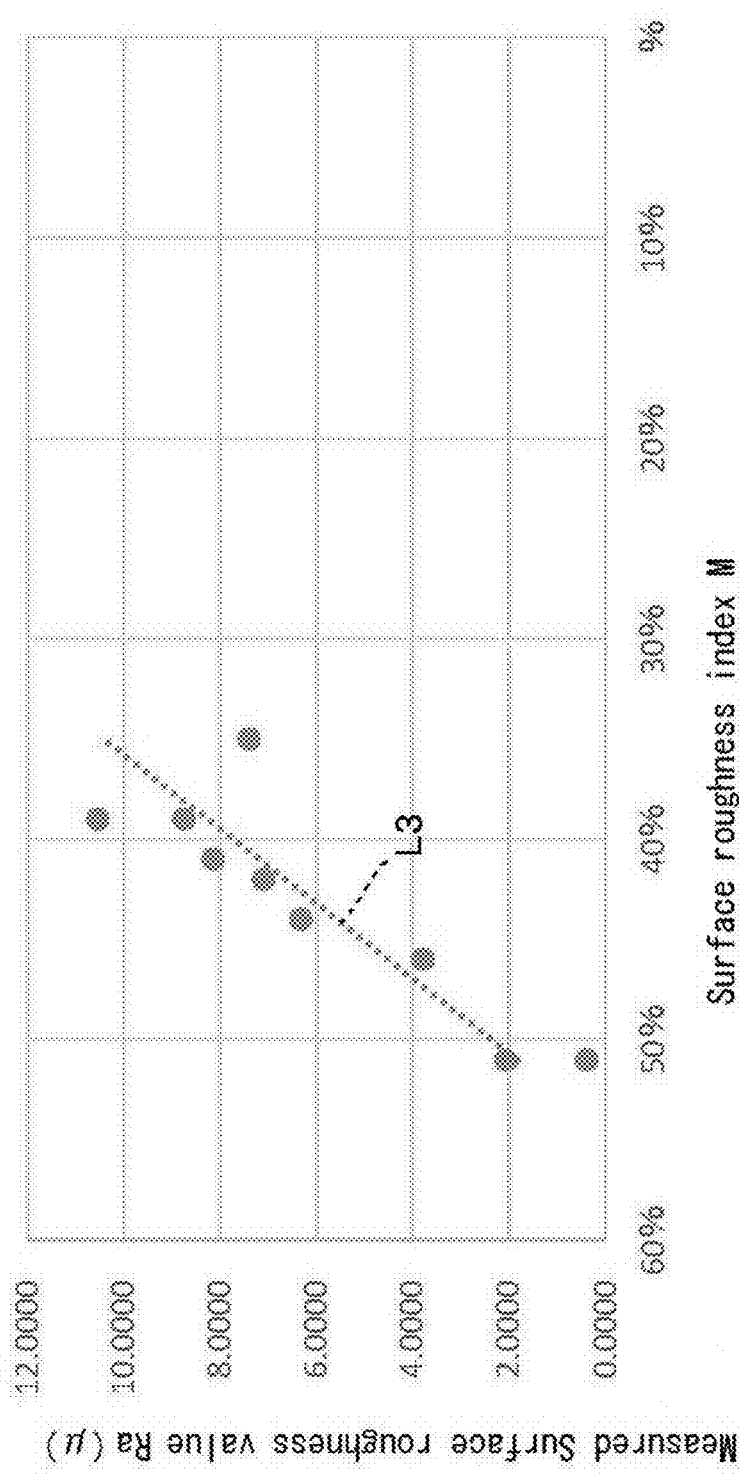
FIG. 25 is a graph 3 showing a variation in measured surface roughness value Ra against surface roughness index M with regard to the metal sample 2 of Example 1.

Table 2 and FIG. 23 to FIG. 25 show the results of measurement of the sample 2 of aluminum alloy and calculation according to Mathematical Expression 6 or the like.

FIG. 23 shows the measured surface roughness value Ra (unit of μm) as the abscissa and the surface roughness estimation index Est as the ordinate, and a dotted straight line is the first calibration curve L1. FIG. 24 shows the color difference ΔE as the abscissa and the measured surface roughness value Ra (unit of μm) as the ordinate, and a dotted straight line is the second calibration curve L2. FIG. 25 shows the surface roughness index M as the abscissa and the measured surface roughness value Ra (unit of μm) as the ordinate, and a dotted straight line is the third calibration curve L3.

TABLE 2

| Sample No. 2 | Index M | ΔE | Ra | Est | Error |
|---|---|---|---|---|---|
| NO. 21 | 51% | 2.879 | 0.3949 | 2.044383 | 1.649483 |
| NO. 22 | 51% | 3.206 | 2.0733 | 2.271415 | 0.198115 |
| NO. 23 | 46% | 3.825 | 3.7892 | 2.696716 | 1.092484 |
| NO. 24 | 44% | 6.532 | 6.3261 | 4.57437 | 1.75173 |
| NO. 25 | 42% | 9.147 | 7.1023 | 6.388149 | 0.714151 |
| NO. 26 | 39% | 10.273 | 8.7501 | 7.167239 | 1.582861 |
| NO. 27 | 41% | 11.978 | 8.1449 | 8.352787 | 0.207887 |
| NO. 28 | 39% | 15.130 | 10.5394 | 10.5394 | 1.67E-06 |
| NO. 29 | 35% | 16.970 | 7.4049 | 11.81332 | 4.408418 |
| | | | | TotErro | 11.60513 |

The results obtained were a=0.000893 and b=0.694288. The correlation coefficient of the surface roughness evaluation index Est and the measured surface roughness value Ra was 0.849651. The correlation coefficient of the color difference ΔE and the measured surface roughness value Ra was 0.849774. The correlation coefficient of the surface roughness index M and the measured surface roughness value Ra was −0.88685. The total error TotErro was 11.60513. FIG. 23 includes one deviated point of Est=8.352787. Exclusion of this point as the measurement error gives the correlation coefficient of approximately 0.9.

In Tables 1 and 2, increasing the etching time of chemical etching of the aluminum alloy from No. 11 to No. 19 or from No. 21 to No. 29 decreases the surface roughness index M and increases ΔE, Ra and Est.

Chemical etching of the aluminum alloy changes the degree of roughness from the originally flat surface 5 to the rough surface 5. Further etching provides various degrees of roughness, for example, forming a hole in the surface 5, forming a recess on the surface 5 or forming a cavity under the surface 5. Such various degrees of roughness were evaluated accurately.

Example 1 uses the first calibration curve L1 to the third calibration curve L3 to accurately calculate the surface roughness in micron-order or in nano-order, to recognize the appropriate irregularities, and to reduce defective products by comparison with reference values. For example, when the aluminum alloy treated by chemical etching is coated with a resin layer, the resin layer is likely to peeled off from the aluminum alloy according to the excess or deficiency of etching. The optimum surface roughness that does not cause the resin layer to be peeled off from the aluminum alloy is determinable by examining the surface 5 of the aluminum alloy prior to coating of the resin on the aluminum alloy. This configuration prevents the resin layer from being peeled off from the aluminum alloy and is highly valuable in the industry.

Example 2

The measurement position, the surface roughness index M, ΔE00, ΔL value, Δa value, Δb value and the like are shown with regard to the sample 3 that is a resin component of Example 2. Multiple regression analysis was performed by the same technique as that of Example 1. Similar results were obtained, although the description is omitted. The measurement range is within frame lines of the images A and B.

Figure 27:
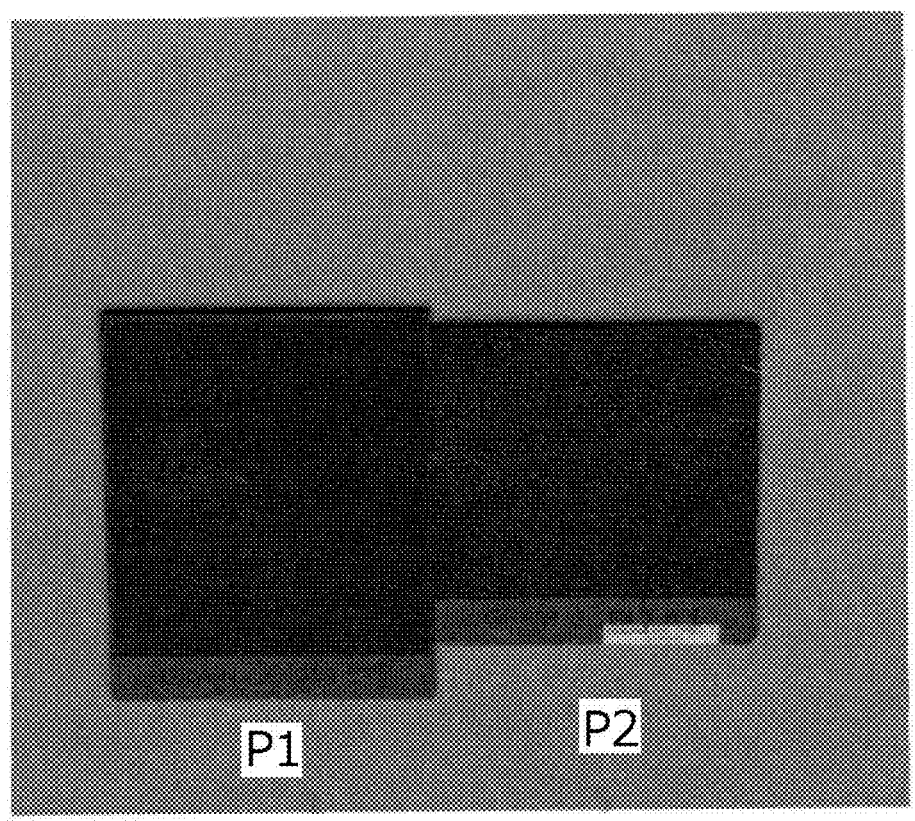
FIG. 27 is a photographic diagram illustrating the resin sample 3 of Example 2.

The sample 3 shown in FIG. 27 was used for quantification of the surface roughness caused by a difference in embossing between two different resins P1 and P2.

The lighting color temperature was 5000 K.

Figure 28:
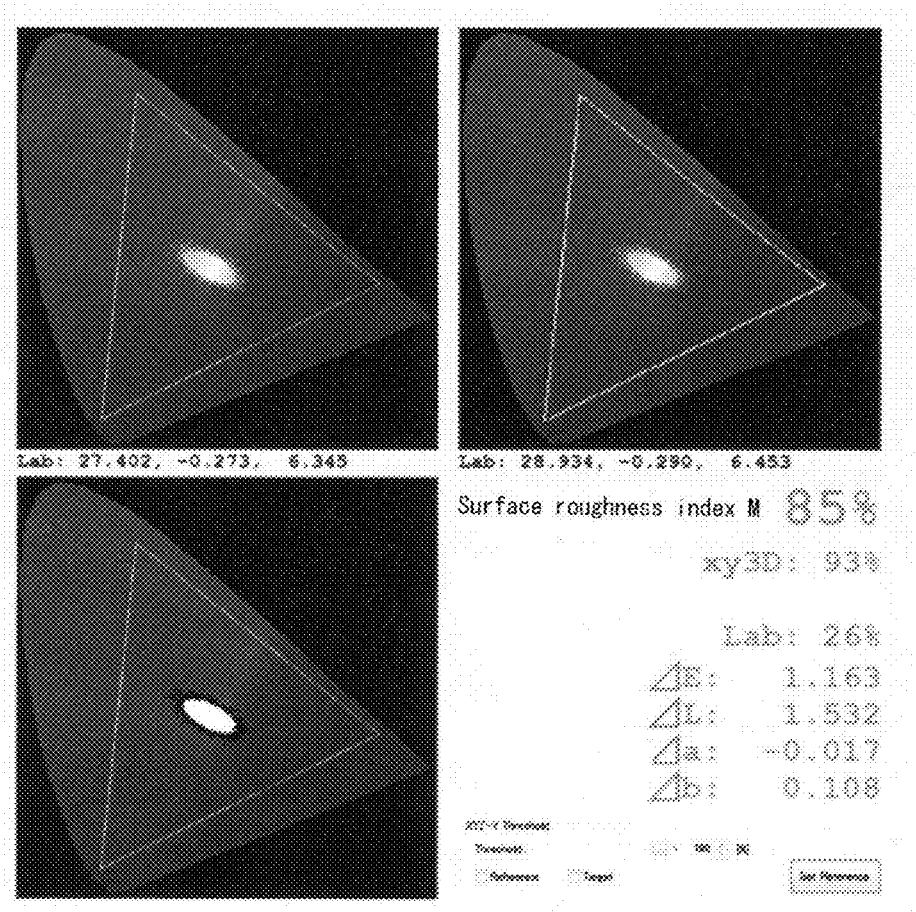
FIG. 28 is photographic diagrams illustrating measurement ranges and measurement positions (within green frames of images) with regard to the resin sample 3 of Example 2.

The results of evaluation of the sample 3 are shown in FIG. 28. The differences of the Lab value and ΔE were detected. The surface roughness index (roughness matching degree) was 85%. The three-dimensional xy matching degree xy3D was 93%. The Lab matching degree of P2 relative to P1 was 26%. This proves clear differentiation of the surface roughness. The color difference ΔE was 1.163, ΔL was 1.532, Δa was −0.017, Δb was 0.108. The high L value of P2 indicates the high lightness. Δa and Δb indicate a difference in color of the material. xy3D is a value obtained by correcting color shift.

Figure 26:
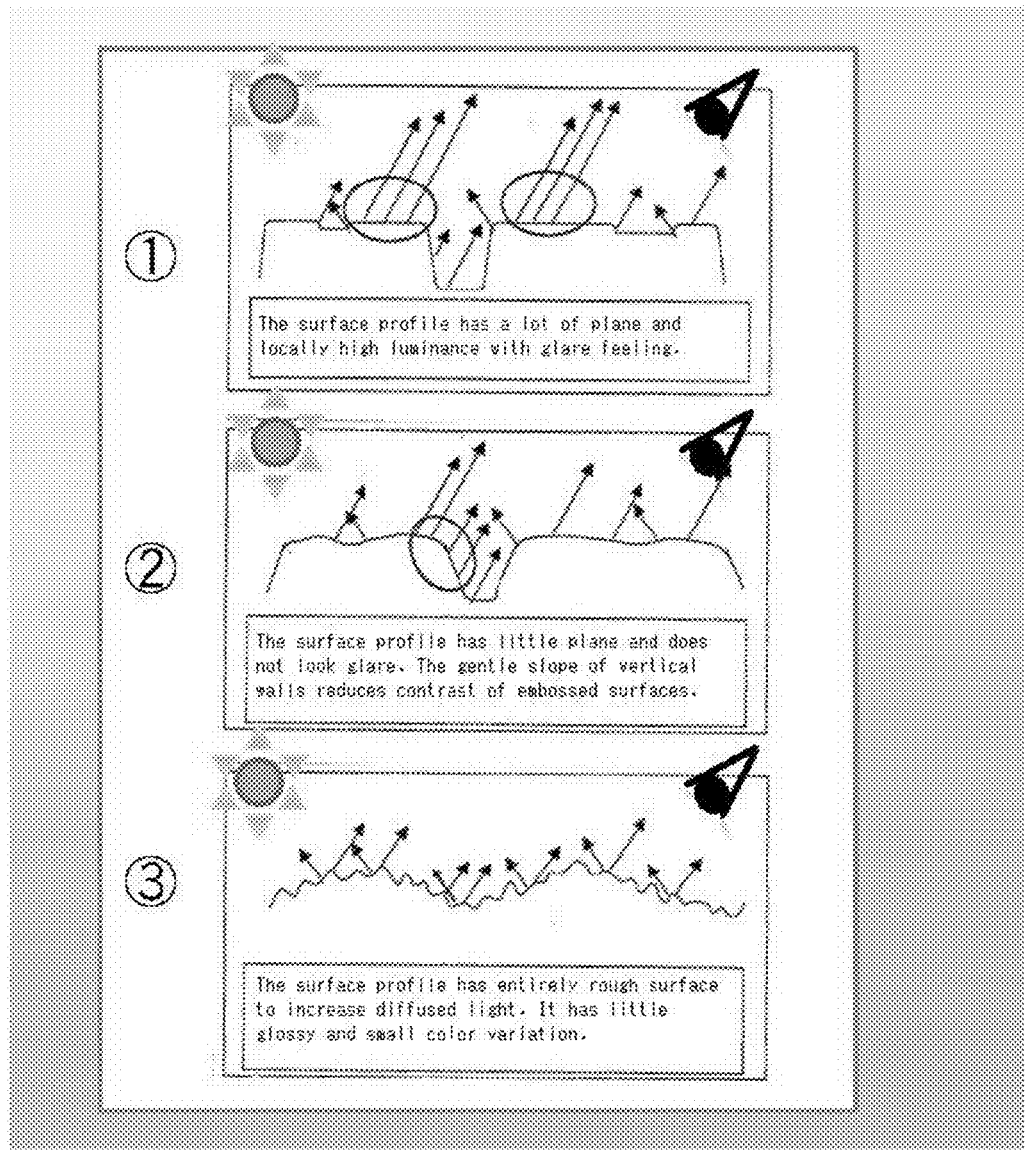
FIG. 26 is a diagram illustrating reflection from surfaces of a resin sample 3 of Example 2.

As shown in FIG. 26, the difference in "appearance" due to the difference in embossing indicates the difference in reflection due to the difference in embossed surface profile. The total reflection part strongly reflects the color of illumination and has the high luminance. Accordingly, the surface profile (1) causes the totally reflected light to locally enter the eye and looks glare. The surface profile (2) has little plane and disperses the total reflection direction. This does not look glare and causes color interference and color expansion by combination of various reflections. The surface profile (3) causes the light to be finely and totally diffused and has the low luminance and the averaged color.

Example 2 uses the surface roughness index M to recognize the appropriate irregularities and reduces defective products by comparison with reference values. For example, in the case of the embossed surface 5 of resin, a subtle change in glaze of the surface 5 is recognizable with regard to the deep embossed surface or the shallow embossed surface, irrespective of the small color difference ΔE. This is applicable to various aspects, for example, reducing defects of embossing and is highly valuable in the industry.

Example 3

Sample 4 of Example 3 shows the example of evaluation of the surface roughness in nano-order with regard to the metal surface of the aluminum alloy. The measured surface roughness value Ra (unit of nm) was measured by using contactless roughness meter VN-8010 manufactured by KEYENCE CORPORATION.

Figure 29:
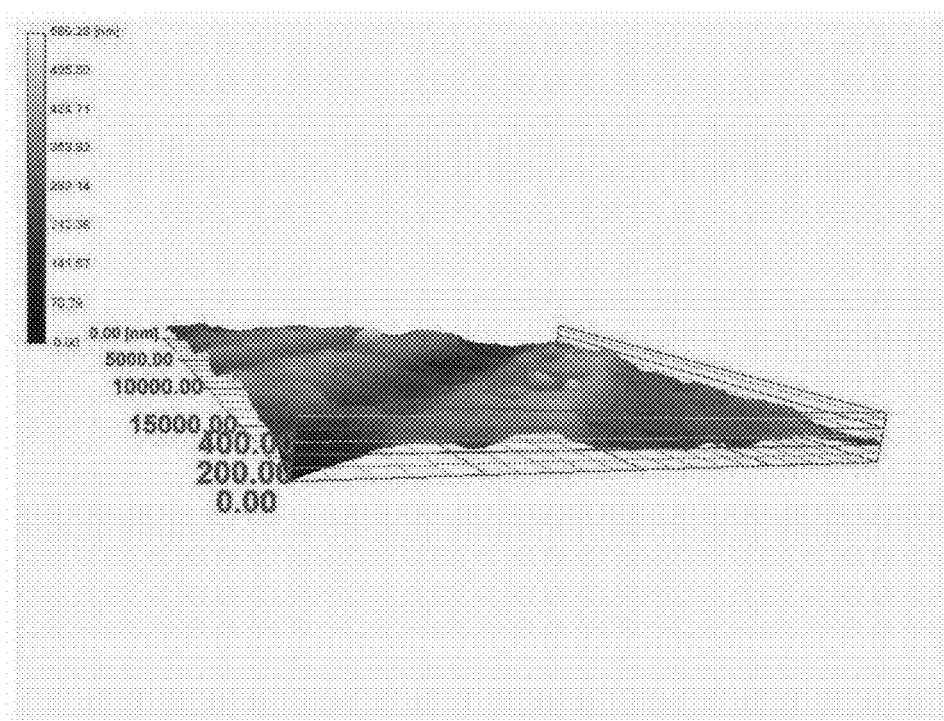
FIG. 29 is a three-dimensional diagram showing the measurement result of AFM with regard to a metal sample No. 41 of Example 3.
Figure 30:
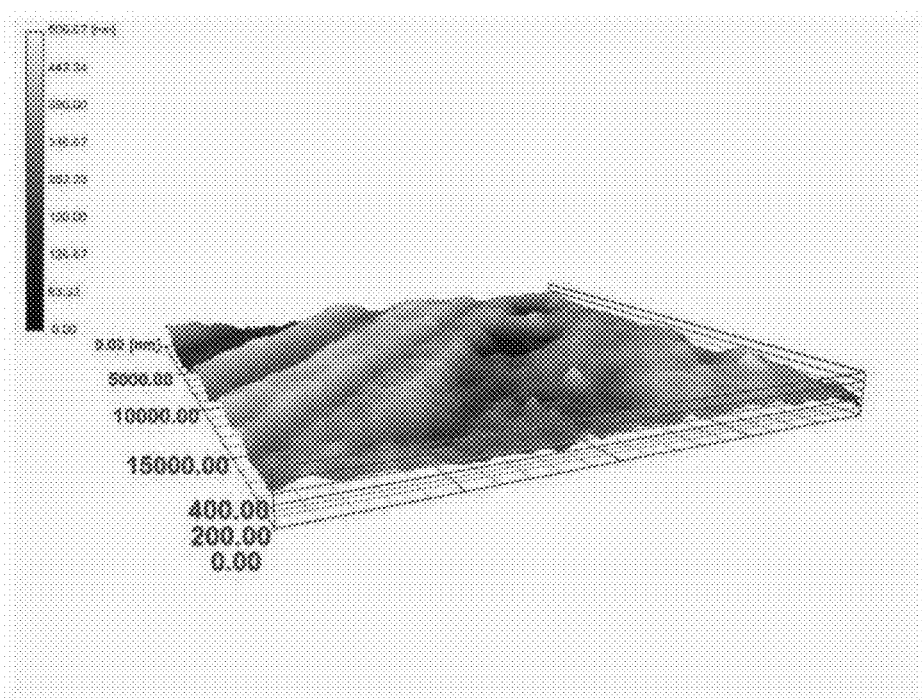
FIG. 30 is a three-dimensional diagram showing the measurement result of AFM with regard to a metal sample No. 42 of Example 3.
Figure 31:
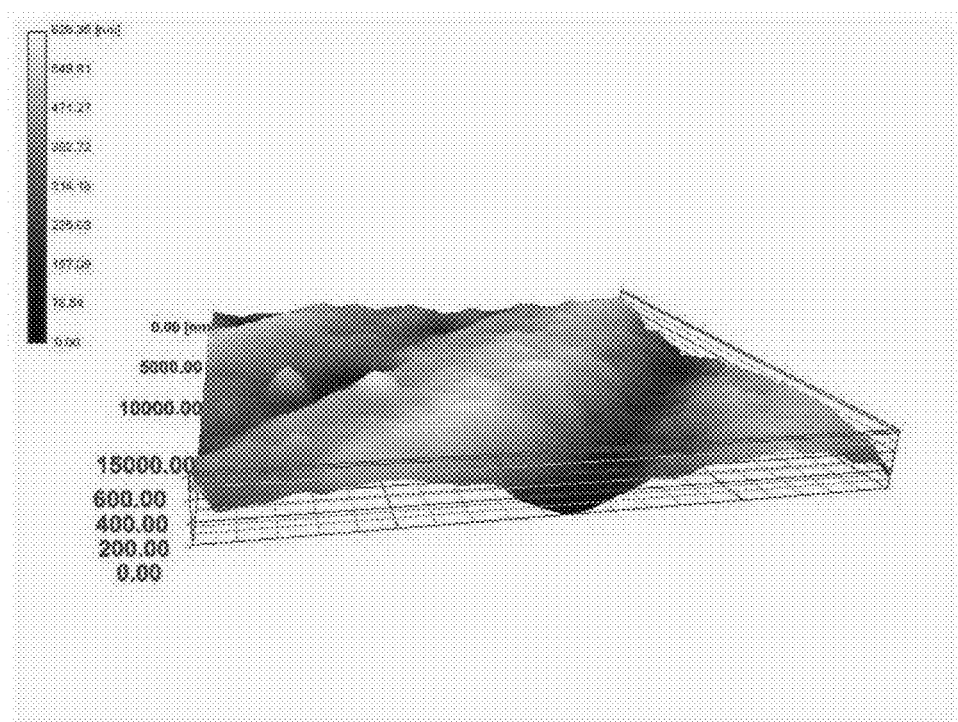
FIG. 31 is a three-dimensional diagram showing the measurement result of AFM with regard to a metal sample No. 43 of Example 3.
Figure 32:
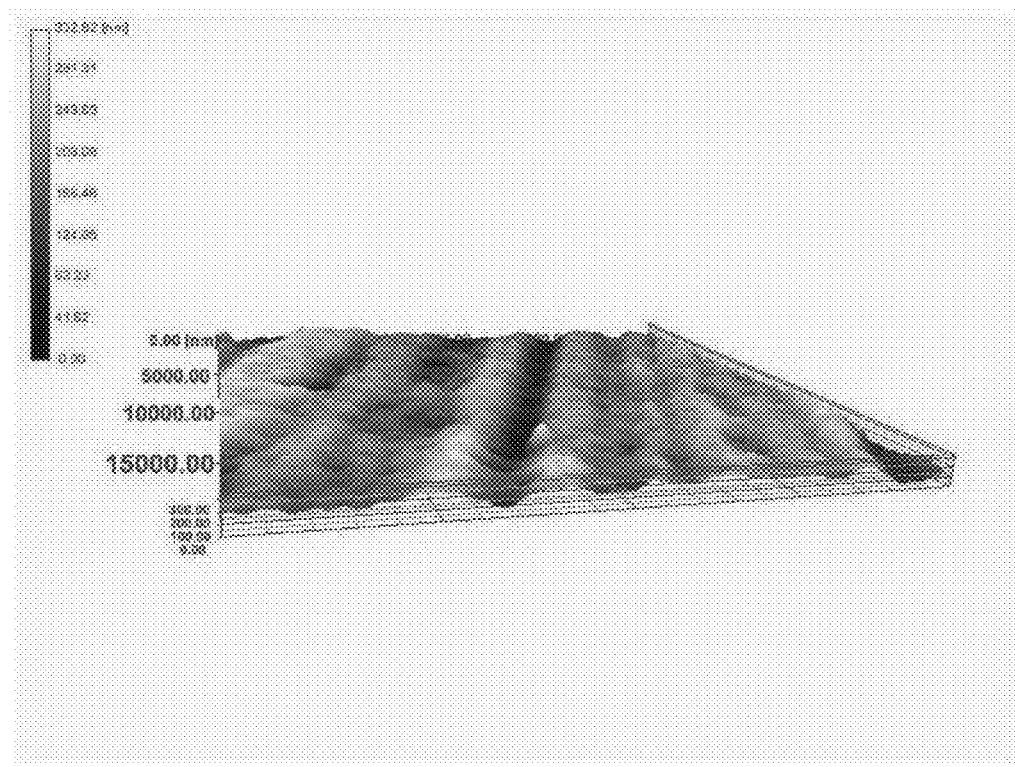
FIG. 32 is a three-dimensional diagram showing the measurement result of AFM with regard to a metal sample No. 44 of Example 3.
Figure 33:
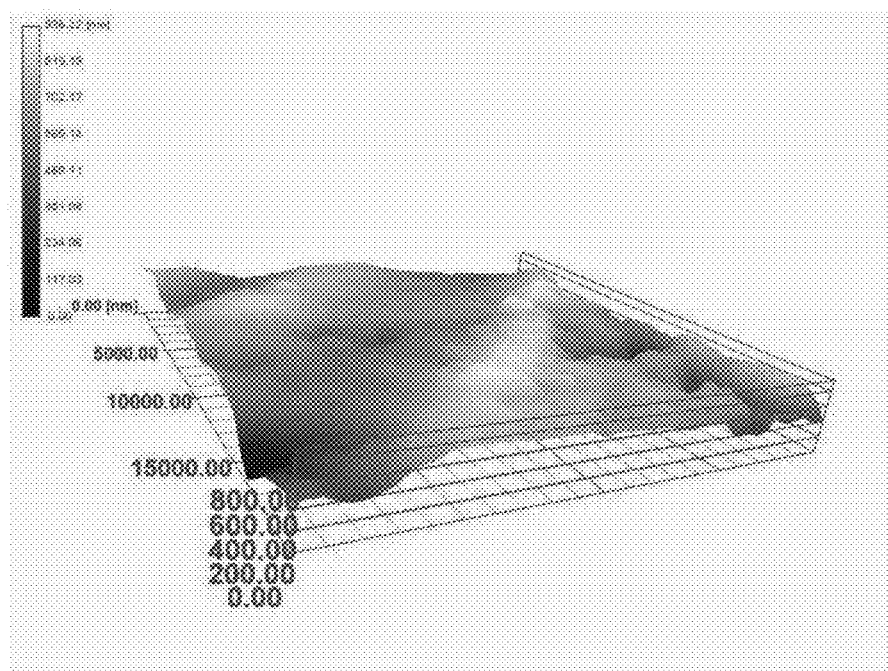
FIG. 33 is a three-dimensional diagram showing the measurement result of AFM with regard to a metal sample No. 45 of Example 3.
Figure 34:
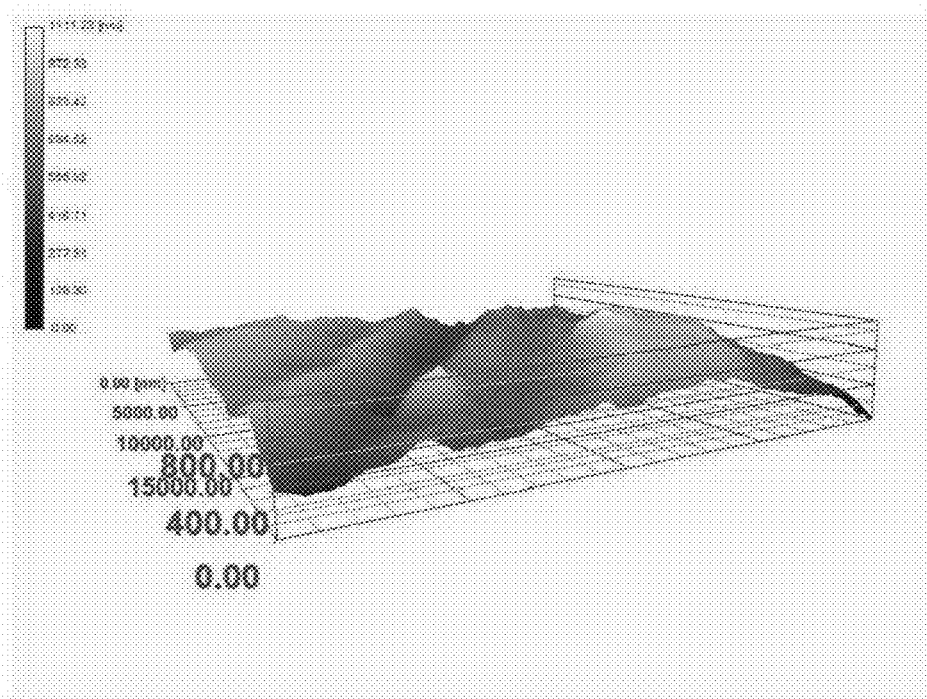
FIG. 34 is a three-dimensional diagram showing the measurement result of AFM with regard to a metal sample No. 46 of Example 3.

Table 3 shows the results of measurement and calculation of the surface roughness index M, the measured surface roughness value Ra, and the surface roughness evaluation index Est. Mathematical Expression 7 was used for calculation in Table 3. FIGS. 29 to 35 are three-dimensional CGs showing the surface irregularities of samples No. 41 to No. 47 with regard to the measured surface roughness value Ra. FIG. 29 shows the average irregularity of 88.33 nm in the total area of the sample No. 41. FIG. 30 shows the average irregularity of 58.83 nm in the total area of the sample No. 42. FIG. 31 shows the average irregularity of 88.33 nm in the total area of the sample No. 43. FIG. 32 shows the average irregularity of 57.71 nm in the total area of the sample No. 44. FIG. 33 shows the average irregularity of 93.9 nm in the total area of the sample No. 45. FIG. 34 shows the average irregularity of 112.85 nm in the total area of the sample No.

Figure 35:
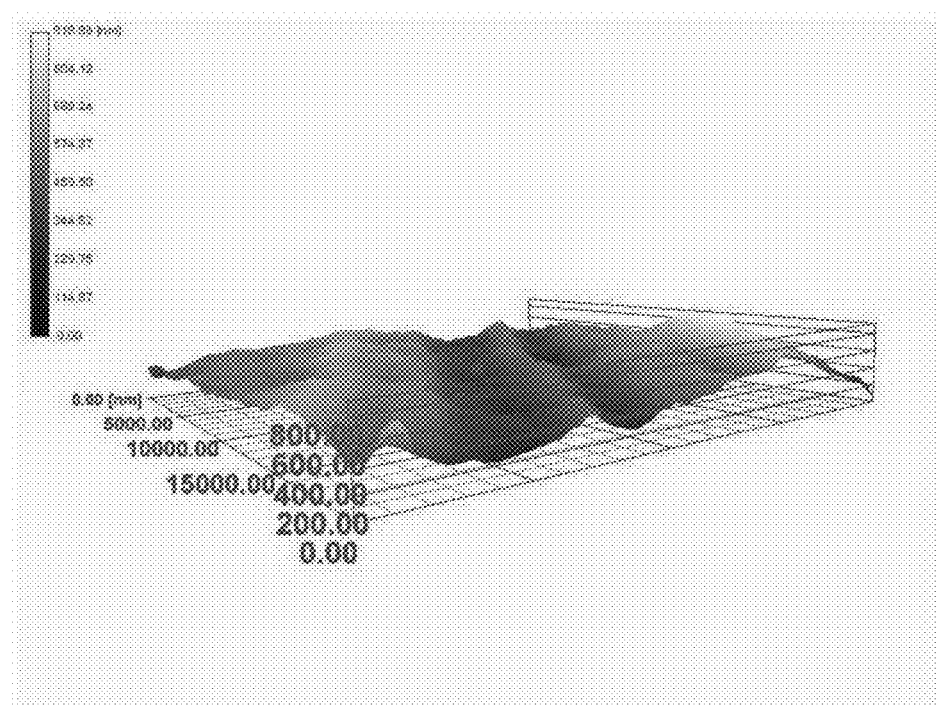
FIG. 35 is a three-dimensional diagram showing the measurement result of AFM with regard to a metal sample No. 47 of Example 3.

46. FIG. 35 shows the average irregularity of 100.18 nm in the total area of the sample No. 47. These values are average values of height from the reference surface and indicate the surface distortion of the averaged irregularity. In ascending order of the sample number from the sample No. 41 to the sample No. 47, the etching time is sequentially increased, and the surface roughness index M decreases and the measured surface roughness value Ra increases.

TABLE 3

| Sample No. 4 | Index M | Surface roughness evaluation index Est | Measured surface roughness value Ra(nm) | Error |
|---|---|---|---|---|
| NO. 41 | 73% | 59.7624398 | 52.82 | 48.19747 |
| NO. 42 | 81% | 51.2341385 | 58.83 | 57.69711 |
| NO. 43 | 58% | 77.1433629 | 88.33 | 125.1409 |
| NO. 44 | 54% | 81.023878 | 57.71 | 543.5369 |
| NO. 45 | 40% | 97.6993687 | 93.9 | 14.4352 |
| NO. 46 | 30% | 109.371202 | 112.85 | 12.10203 |
| NO. 47 | 48% | 88.3848691 | 100.18 | 139.1251 |
| | | | Error | 940.2347 |

The results obtained were a=1.141439 and b=143.1954. The total error TotErro was 940.2347.

Figure 36:
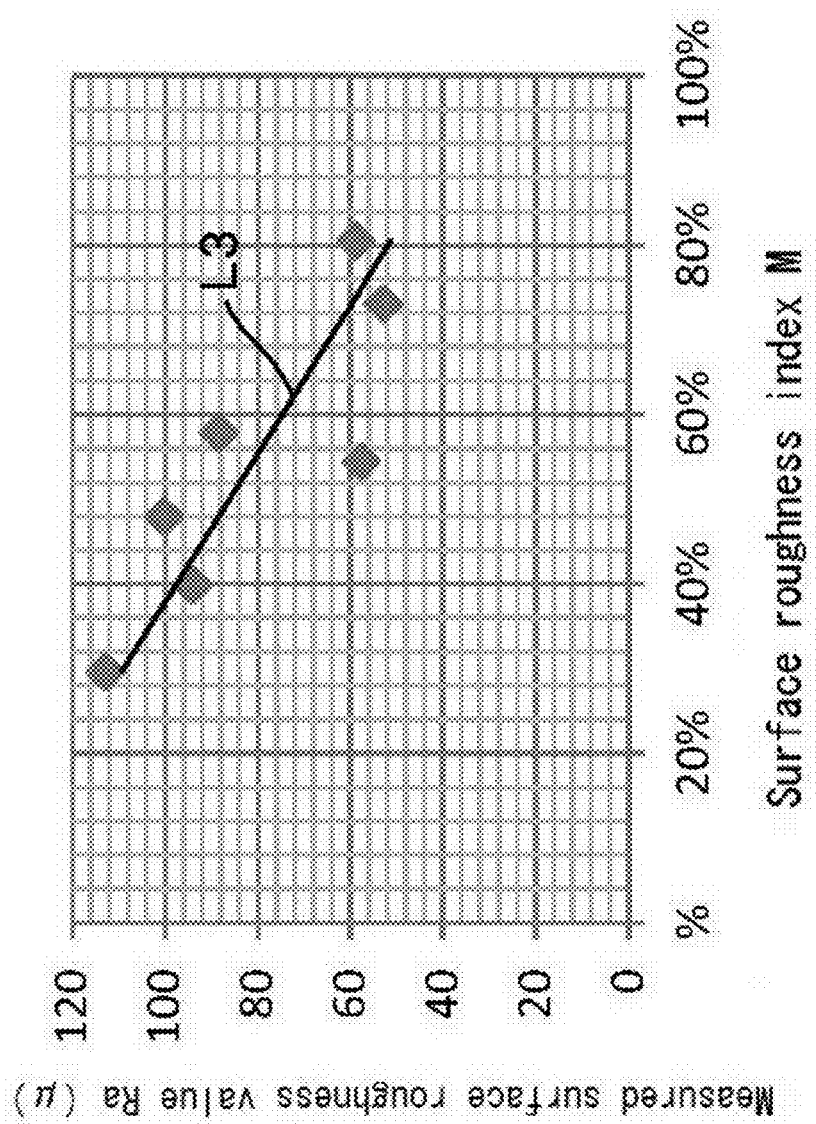
FIG. 36 is a graph 1 showing a relationship between the surface roughness index M and the measured surface roughness value Ra of Example 3.
Figure 37:
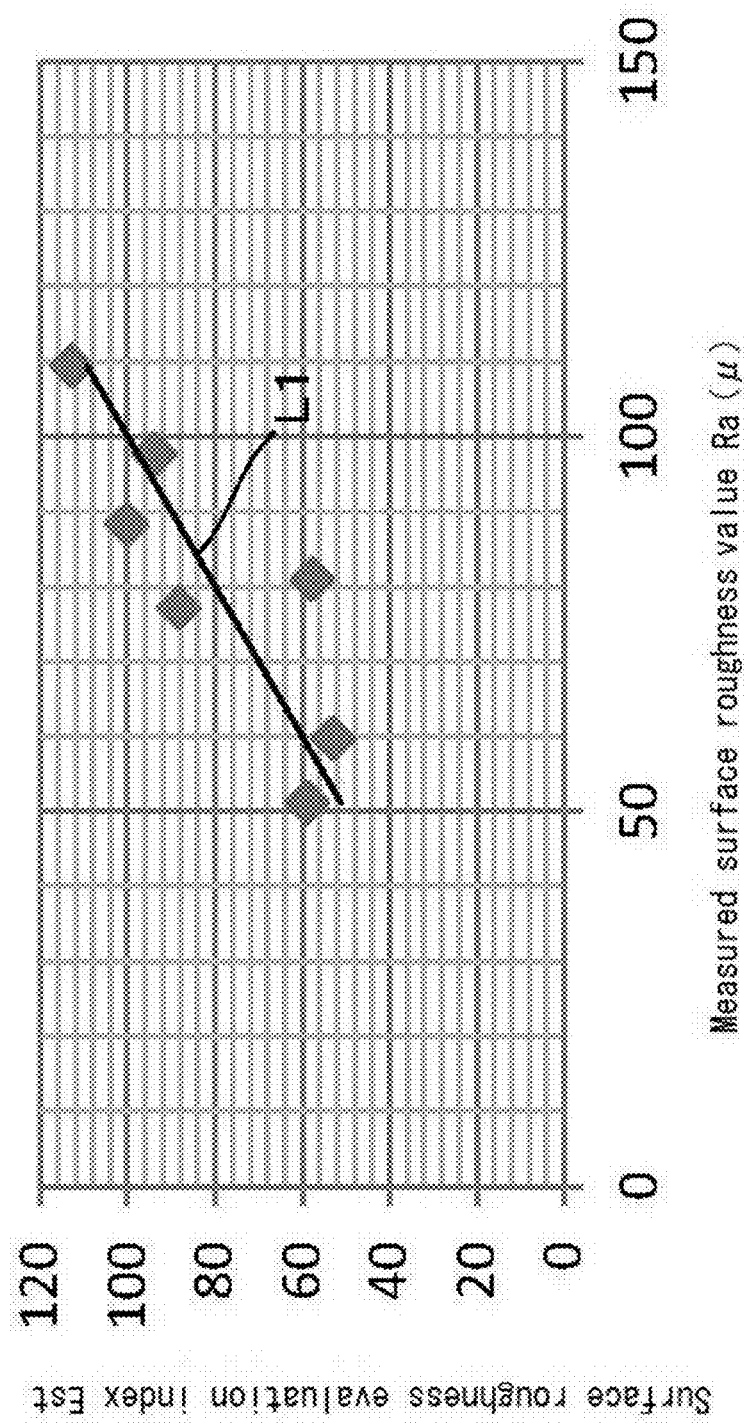
FIG. 37 is a graph 2 showing a variation in surface roughness evaluation index Est against measured surface roughness value Ra with regard to the metal samples No. 41 to No. 47 of Example 3.

Example 3 uses the first calibration curve L1 shown in FIG. 37 and the third calibration curve L3 shown in FIG. 36 to recognize the appropriate irregularities, evaluate the surface roughness in nano-order and reduce defective products.

Example 4 is an example to determine a surface roughness of a metallic surface of aluminum alloy in nano-order. Measured surface roughness value Ra (unit of μm) is measured by a mechanical type roughness meter (FORM TALYSURF (registered trademark) manufactured by Taylor Hobson) using metallic roughness standard samples of different materials as calibration plates. It is because it is necessary to calculate values with a correction to offset base colors when the metallic intrinsic colors of the roughness standard samples and an object to be measured are different. FIG. 38 shows measurement data.

When the metallic material of the object to be measured is the same as the material of the calibration plates, surface roughness index M without offset is calculated, and Ra value is calculated from the surface roughness index M. Calibration values are prescribed in JIS. For example, a calibration curve is made using the least-square method.

When the metallic material of the object to be measured is not known, surface roughness index M with offset correction is calculated as described in Embodiment 4, and the surface roughness index M is converted to Ra value by a fourth calibration curve.

The fourth calibration curve for the data shown in FIG. 38 was calculated to be Mathematical Expression 9.

$$Ra=62.31/(M-18.526) \quad \text{[Math. 9]}$$

where, Ra is measured surface roughness value Ra (arithmetically averaged roughness), M is surface roughness index.

Measured surface roughness values Ra of the graph shown in FIG. 38 is obtained by measuring different roughness surfaces of eight kinds of roughness standard samples.

Figure 39:
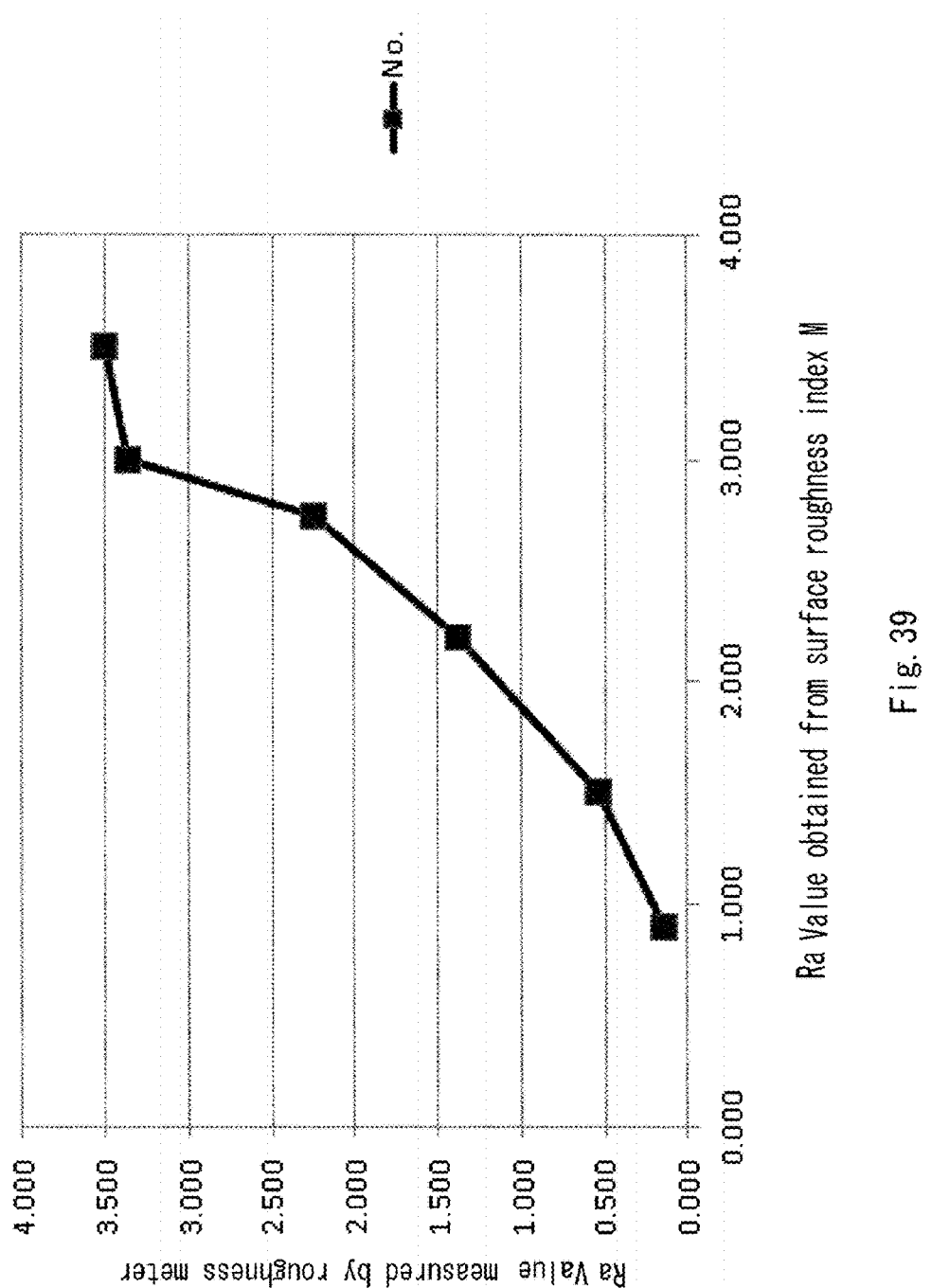
FIG. 39 is a graph showing a variation in Ra value measured by a roughness meter against Ra value calculated from surface roughness index M in Example 4.

Table 4 shows Ra values calculated from surface roughness index M with offset operation using the fourth calibration curve and Ra values measured by a roughness meter (FORM TALYSURF (registered trademark) manufactured by Taylor Hobson) using another method, with regard to 6 measurement objects. FIG. 39 shows the graph of these data and a calibration curve made using the least-square method.

TABLE 4

| Sample No. | Index M | Ra value calculated from surface roughness index | Ra value measured from roughness meter (by another method) | Error of Ra |
|---|---|---|---|---|
| No. 1 | 80 | 0.900 | 0.150 | 0.750 |
| No. 2 | 66 | 1.500 | 0.548 | 0.750 |
| No. 3 | 53 | 2.200 | 1.380 | 0.952 |
| No. 4 | 45 | 2.750 | 2.252 | 0.820 |
| No. 5 | 43 | 3.000 | 3.372 | 0.498 |
| No. 6 | 38 | 3.500 | 3.510 | 0.372 |

Error of Ra was not greater than 0.75, and a good result was obtained in Example 4.

The present disclosure is not limited to the embodiments described above but may be changed, modified and altered without departing from the scope of the present disclosure. Such modifications and equivalents are also included in the scope of the present disclosure. The present disclosure may be implemented by various configurations in the scope of the present disclosure. For example, the methods of obtaining the images A and B with the three spectral sensitivities (S1(λ), S2(λ) and S3(λ)) described in the above embodiments are only some specific examples. These are not restrictive in any sense. The present disclosure may be implemented by other methods.

INDUSTRIAL APPLICABILITY

The determination apparatus of the present disclosure quantifies the surface roughness by scattering and diffraction of the illumination light and accordingly allows for determination extremely close to human visual determination. This is applicable to evaluation of the surface roughness that generally depends on the human vision. The present disclosure is applicable to a wide variety of materials including metals and resins and various surfaces including flat surfaces, curved surfaces and surfaces of complicated shapes.

REFERENCE SIGNS LIST 1, 101, 201 surface roughness determination apparatus
2, 102, 202 two-dimensional colorimeter
21 imaging lens
22a, 22b, 22c optical filters
23 imaging element
22a', 22c' dichroic mirrors
23a, 23b, 23c imaging elements
26 reflector
27 filter turret
3, 103, 203 arithmetic processing unit
5, 105, 205 surface
6, 106, 206 lighting unit
7 display device
109 switch
250 roughness processing unit
a first coefficient
b second coefficient
A, B images
AFM atomic force microscope
C1, C2 center coordinates
D overlap area
ΔE color difference Error error
Est surface roughness evaluation index
G grid
M surface roughness index
H1, H2 integrated numbers
K examination area
T examination area
TotErro total error

The invention claimed is:

1. A surface roughness determination apparatus using a white light source, the apparatus comprising:
   an imaging device configured to have three spectral sensitivities (S1($\lambda$), S2($\lambda$), and S3($\lambda$)) subjected to linear transformation so as to be equivalent to a CIE XYZ color matching function and to obtain 3-band visual sensitivity images S1$i$, S2$i$ and S3$i$; and
   an arithmetic processing unit connected to the image device, the arithmetic processing unit configured to:
      convert the 3-band visual sensitivity images S1$i$, S2$i$ and S3$i$ into tristimulus values X, Y and Z in a CIE XYZ color system,
      calculate a color difference $\Delta E$,
      divide an examination area of coordinates corresponding to a color space in the CIE XYZ color system by grids and respectively integrate the numbers of pixels on a test surface and on a reference surface included in each of the grids, so as to create color space histogram distributions in the CIE XYZ color system,
      calculate a surface roughness index M indicating a difference between the two color space histogram distributions of the test surface and the reference surface with or without an offset correction,
      store a measured surface roughness value Ra measured by a roughness meter, and
      set at least one of a first calibration curve function indicating a correlation of the measured surface roughness value Ra to a surface roughness evaluation index Est, a second calibration curve function indicating a correlation of the measured surface roughness value Ra to the color difference $\Delta E$, a third calibration curve function indicating a correlation of the measured surface roughness value Ra to the surface roughness index M calculated without the offset correction, or a fourth calibration curve function indicating a correlation of the measured surface roughness value Ra to the surface roughness index M calculated with the offset correction, to enable accurate determination of a surface roughness.

2. The surface roughness determination apparatus using a white light source, according to claim 1,
   wherein the offset correction is performed by specifying the centers of the two color space histogram distributions of the test surface and the reference surface, and offsetting so as to bring one of the centers of the color space histogram distributions close to the other center of the color space histogram distribution.

3. The surface roughness determination apparatus using a white light source, according to claim 1,
   wherein the surface roughness evaluation index Est is determined by specifying a first coefficient with regard to the surface roughness index and a second coefficient with regard to the color difference, so as to minimize an error between the surface roughness evaluation index Est and the measured surface roughness value Ra.

4. A surface roughness determination method using a white light source, the method comprising:
   converting, by an arithmetic processing unit, 3-band visual sensitivity images S1$i$, S2$i$ and S3$i$, which respectively have three spectral sensitivities (S1($\lambda$), S2($\lambda$) and S3($\lambda$)) subjected to linear transformation so as to be equivalent to a CIE XYZ color matching function and are obtained by an imaging device using the three spectral sensitivities (S1($\lambda$), S2($\lambda$) and S3($\lambda$)), into tristimulus values X, Y and Z in a CIE XYZ color system and performing arithmetic operations,
   calculating, by the arithmetic processing unit, a color difference $\Delta E$;
   dividing, by the arithmetic processing unit, an examination area of coordinates corresponding to a color space in the CIE XYZ color system by grids and respectively integrating the numbers of pixels on a test surface and on a reference surface included in each of the grids, so as to create color space histogram distributions in the CIE XYZ color system;
   calculating, by the arithmetic processing unit, a surface roughness index M indicating a difference between the two color space histogram distributions of the test surface and the reference surface with or without an offset correction;
   storing, by the arithmetic processing unit, a measured surface roughness value Ra measured by a roughness meter; and
   setting, by the arithmetic processing unit, at least one of a first calibration curve function indicating a correlation of the measured surface roughness value Ra to a surface roughness evaluation index Est, a second calibration curve function indicating a correlation of the measured surface roughness value Ra to the color difference $\Delta E$, a third calibration curve function indicating a correlation of the measured surface roughness value Ra to the surface roughness index M calculated without the offset correction, or a fourth calibration curve function indicating a correlation of the measured surface roughness value Ra to the surface roughness index M calculated with the offset correction, to enable accurate determination of a surface roughness.

5. The surface roughness determination method using a white light source, according to claim 4,
   wherein the offset correction is performed by specifying the centers of the two color space histogram distributions of the test surface and the reference surface, and offsetting so as to bring one of the centers of the color space histogram distributions close to the other center of the color space histogram distribution.

6. The surface roughness determination method using a white light source, according to claim 4,
   wherein the surface roughness evaluation index Est is determined by specifying a first coefficient with regard to the surface roughness index and a second coefficient with regard to the color difference, so as to minimize an error between the surface roughness evaluation index Est and the measured surface roughness value Ra.

* * * * *